US010290103B2

(12) United States Patent
Warntjes

(10) Patent No.: US 10,290,103 B2
(45) Date of Patent: May 14, 2019

(54) METHOD, DEVICE AND NON-TRANSITORY DIGITAL STORAGE MEDIUM FOR NON-AQUEOUS TISSUE VOLUME ESTIMATION

(71) Applicant: Synthetic MR AB, Linköping (SE)

(72) Inventor: Marcel Warntjes, Ljungsbro (SE)

(73) Assignee: Synthetic MR AB, Linkoping (SE)

( * ) Notice: Subject to any disclaimer, the term of this patent is extended or adjusted under 35 U.S.C. 154(b) by 239 days.

(21) Appl. No.: 15/166,239

(22) Filed: May 26, 2016

(65) Prior Publication Data
US 2017/0345149 A1    Nov. 30, 2017

(51) Int. Cl.
| G06K 9/00 | (2006.01) |
| G06T 7/00 | (2017.01) |
| A61B 5/055 | (2006.01) |
| A61B 5/00 | (2006.01) |
| G01R 33/48 | (2006.01) |
| G01R 33/50 | (2006.01) |
| G01R 33/56 | (2006.01) |

(52) U.S. Cl.
CPC ............ *G06T 7/0014* (2013.01); *A61B 5/055* (2013.01); *A61B 5/4875* (2013.01); *G01R 33/4828* (2013.01); *G01R 33/50* (2013.01); *G01R 33/5608* (2013.01); *G06T 2207/10088* (2013.01); *G06T 2207/30016* (2013.01)

(58) Field of Classification Search
None
See application file for complete search history.

(56) References Cited

U.S. PATENT DOCUMENTS

| 4,634,979 A | 1/1987 | Riederer et al. |
| 4,641,095 A | 2/1987 | Riederer |
| 4,881,033 A | 11/1989 | Denison et al. |
| 5,262,945 A | 11/1993 | DeCarli et al. |
| 5,486,763 A | 1/1996 | Alfano |
| 6,366,797 B1 | 4/2002 | Fisher et al. |
| 6,823,205 B1 | 11/2004 | Jara |
| 6,917,199 B2 | 7/2005 | Jara |
| 7,002,345 B2 | 2/2006 | Jara |
| 7,973,530 B2 | 7/2011 | Warntjes |
| 8,289,329 B2 | 10/2012 | Warntjes |

(Continued)

FOREIGN PATENT DOCUMENTS

| WO | 2011/114264 A1 | 9/2011 |
| WO | 2016/035205 A1 | 3/2015 |

OTHER PUBLICATIONS

R. Maitra et al., Bayesian Reconstruction in Synthetic Magnetic Resonance Imaging, Proc. SPIE, 1998, pp. 39-47, vol. 3459.

(Continued)

*Primary Examiner* — Atiba O Fitzpatrick
(74) *Attorney, Agent, or Firm* — Oblon, McClelland, Maier & Neustadt LLP

(57) ABSTRACT

A method, device and non-transitory digital storage medium for estimating non-aqueous tissue volume of at least a portion of a subject. The method includes, in a processing unit, obtaining quantitative magnetic resonance properties of the portion of the subject, providing the quantitative magnetic resonance properties as input to a tissue model, and determining the non-aqueous tissue volume of the portion based on the tissue model and the quantitative magnetic resonance properties.

18 Claims, 11 Drawing Sheets

(56) References Cited

U.S. PATENT DOCUMENTS

| | | |
|---|---|---|
| 8,643,363 B2 | 2/2014 | Warntjes |
| 8,873,822 B2 | 10/2014 | Warntjes |
| 8,874,189 B2 | 10/2014 | Warntjes |
| 9,041,393 B2 | 5/2015 | Warntjes |
| 2007/0167727 A1 | 7/2007 | Menezes et al. |
| 2008/0292194 A1 | 11/2008 | Schmidt |
| 2009/0312625 A1 | 12/2009 | Du |
| 2010/0166284 A1 | 7/2010 | Smith et al. |
| 2014/0002076 A1 | 1/2014 | Warntjes |
| 2014/0180061 A1* | 6/2014 | Warntjes ............ G01R 33/50 600/416 |
| 2015/0073258 A1* | 3/2015 | Mazer ............... G01R 33/50 600/410 |
| 2015/0177350 A1 | 6/2015 | Warntjes |
| 2015/0301140 A1* | 10/2015 | Lee ............... G01R 33/5602 324/309 |

OTHER PUBLICATIONS

M. Prastawa et al., Synthetic Ground Truth for Validation of Brain Tumor MRI Segmentation, Med Image Comput Comput Assist Interv., 2005, pp. 26-33, 8 (Pt 1).

K.H. Cheng et al., In-vivo Tissue Characterization of Brain by Synthetic MR Proton Relaxation and Statistical Chisquares Parameter Maps, Proc. 8th Symposium on Computer-Based Medical Systems, 1995, pp. 338-345, IEEE.

M. Warntjes et al., Rapid Magnetic Resonance Quantification on the Brain: Optimization for Clinical Usage, Magnetic Resonance in Medicine, 2008, pp. 320-329, vol. 60, Wiley-Liss, Inc.

B. Grassiot et al., Quantification and Clinical Relevance of Brain Atrophy in Multiple Sclerosis: A Review, J. Neurol., 2009, pp. 1397-1412, vol. 256, Springer.

J. West et al., Novel Whole Brain Segmentation and Volume Estimation Using Quantitative MRI, Eur. Radial., Nov. 24, 2011, pp. 1-10, Springer.

R. Levesque and G.B. Pike, Characterizing White Matter Pathology with Quantitative Magnetization Transfer Imaging: Insight from a Four-Pool Model, Proc. Int'l Soc. Mag. Reson. Med., Apr. 18, 2009, p. 182, vol. 17.

Stehning et al., Volumetric Simultaneous T1, T2, T2 and Proton Density Mapping in One Minute Using Interleaved Inversion Recovery SSFP and Multi Gradient Echo Imaging, Proc. Int'l Soc. Magnetic Resonance in Medicine, Apr. 16, 2008, p. 241, vol. 16, Toronto, CA.

Markl et al., Gradient Echo Imaging, J. Magnetic Resonance Imaging, Jun. 15, 2012, pp. 1274-1289, vol. 35, No. 6, Wiley Periodicals, Inc.

M. Warntjes et al., Modeling the Presence of Myelin and Edema in the Brain Based on Multi-Parametric Quantitative MRI, Frontiers in Neurology, Feb. 17, 2016, pp. 1-15, vol. 7, art. 16.

* cited by examiner ated based on the measurable tissue volume with the measurable tissue volume.

METHOD, DEVICE AND NON-TRANSITORY DIGITAL STORAGE MEDIUM FOR NON-AQUEOUS TISSUE VOLUME ESTIMATION

TECHNICAL FIELD

The present disclosure relates to a method, device and non-transitory digital storage medium for estimating the non-aqueous tissue volume based on Magnetic Resonance Imaging, which can be used to monitor tissue volume in patients, independent of under or over hydration.

BACKGROUND

Magnetic Resonance Imaging (MRI) can generate cross-sectional images in any plane (including oblique planes) of the human body. Medical MRI most frequently relies on the relaxation properties of excited hydrogen nuclei (protons) in water and fat. When the object to be imaged is placed in a powerful, uniform magnetic field the spins of the atomic nuclei with non-integer spin numbers within the tissue all align either parallel to the magnetic field or anti-parallel. The output result of an MRI scan is an MRI contrast image or a series of MRI contrast images.

Many neurological diseases, such as Alzheimer's disease or multiple sclerosis (MS), lead to brain atrophy, i.e. a loss of brain tissue volume in a faster rate than normal. It is interesting to monitor the brain volume evolution of these patients having such diseases to determine the severity of the disease and the impact of treatment. Generally the brain volume is normalized with the intracranial volume to minimize the effect of head size or incomplete acquisition coverage with the imaging modality. The ratio of the brain parenchymal volume (BPV) and the intracranial volume (ICV) is called the brain parenchymal fraction (BPF) and is considered a measure for brain atrophy (see e.g. Grassiot B, et al. Quantification and clinical relevance of brain atrophy in multiple sclerosis: a review. J Neurol 2009; 256:1397-1412).

Further, neuromuscular diseases may cause muscular dystrophy by cell atrophy in the muscular tissue. Therefore, monitoring the gradual change in muscle tissue volume may be of interest to determine the severity of the disease and the impact of any treatment being performed.

In addition to that, monitoring changes in other types of tissues such as internal organs, e.g. liver, kidneys and so on may also be of interest. In fact, such monitoring may be of use concerning all types of soft tissues, i.e. tissues of the body which are not hard tissue such as bone.

An issue for monitoring patients is that tissue may be under or over hydrated. With a reduction of water content the measurable tissue volume will decrease and with a surplus of water content the measurable tissue volume will increase. The hydration state may vary in time, therefore providing an additional variable that obscures the 'true' volume of the tissue. This issue may affect monitoring brain atrophy in neuro-degenerative diseases: a brain may for example be swollen due to inflammatory processes or drinking of the patient. Another example is muscle atrophy in musculoskeletal diseases, where muscle volume may appear to decrease due to dehydration of the patient.

To be able to estimate non-aqueous tissue volume of an object while taking into account the above mentioned drawbacks would therefore be desirable.

SUMMARY

It is an object to provide a method, device and non-transitory digital storage medium to address at least parts of the problems outlined above. This object and potentially others are obtained by the subject-matter as set out in the appended claims.

According to a first aspect a method for estimating non-aqueous tissue volume of at least a portion of a subject is provided. The method comprising, in a processing unit: obtaining quantitative magnetic resonance properties of the portion of the subject, providing the quantitative magnetic resonance properties as input to a tissue model, determining, based on the tissue model and the quantitative magnetic resonance properties, the non-aqueous tissue volume of the portion.

The processing unit may perform the steps sequentially. Between each step there may be additional actions being performed by the processing unit such as storing data or sending data to remote units etc.

The subject may be a human being. The portion being examined may be any part of the body such as an intracranial portion, a muscle portion, a portion of an internal organ and so on. The portion has a volume of at least one voxel.

The tissue model to be used may be predefined, selected by a user or selected by the processing unit. The tissue model is selected from a number of different tissue models based on the portion being examined. Depending on where in the subject the portion is situated, an appropriate tissue model for the type of tissue being examined is to be used.

A user may select an appropriate tissue model based on what is to be examined by MRI, such as an intracranial portion or a knee. Alternatively, the processing unit may select the tissue model based on which type of tissue or the like is detected within the portion. For example, if grey or white matter is detected a tissue model appropriate for the brain may be selected, or if muscle and fat tissue is detected, a tissue model appropriate for examining muscle tissue may be selected.

Determining the non-aqueous tissue volume may comprise: determining at least one partial volume compartment within the portion, and determining a non-aqueous tissue partial volume present within each partial volume compartment, and determining the non-aqueous tissue volume by adding up all said non-aqueous tissue partial volumes, or determining an aqueous partial volume present within each partial volume compartment, and determining a total aqueous volume by adding up all said aqueous partial volumes, and determining the non-aqueous tissue volume by subtracting the total aqueous volume from a total volume of the portion.

A portion comprises at least one partial volume compartment. The partial volume compartment may comprise e.g. tissue or aqueous content. If the partial volume compartment comprises tissue, a certain volume fraction of the tissue is aqueous content, such as intra- and intercellular water for example. Therefore, after determining the partial volume compartment, it is determined to which extent (preferably in terms of volume) the partial volume compartment comprises tissue. Or, it may be determined to which extent the partial volume compartment comprises aqueous content. In case the partial volume compartment comprises aqueous content, such as free water for example, the total volume of the partial volume compartment is determined to be the aqueous partial volume.

The total volume of the portion may for example be predefined or determined by the processing unit in a number of ways. As mentioned above, it may be the volume of one or more voxels.

The partial volume compartment may for example comprise free water, excess parenchymal water, cellular tissue or myelin tissue.

Free water is aqueous content having no magnetization exchange with any other type of volume such as tissue volume. Free water is not included within the tissue, but instead it may be surrounding the tissue such as cerebrospinal fluid, or be confined in vessels, such as blood. The excess parenchymal water may be aqueous content due to an edema. Cellular tissue comprises cells as well as an aqueous fraction that may comprise both intracellular and intercellular water. Myelin tissue comprises myelin as well as myelin water which is aqueous content trapped between the myelin sheaths.

The method may for example be used for estimating the non-aqueous tissue volume of at least a portion of a brain. In that case, each MRI acquisition voxel is composed of four partial volume compartments: the myelin partial volume $V_{MY}$, cellular partial volume $V_{CL}$, free water partial volume $V_{FW}$ and excess parenchymal water partial volume $V_{EPW}$.

A reference value may be provided and the non-aqueous tissue volume may be compared to the reference value.

The reference value may be predetermined. It may be determined from a group of reference subjects. The comparison may be performed by the processing unit or by a user, such as a clinician. The reference value may be a single value, a plurality of values, a range or several ranges of values.

Determining the partial volume compartment may comprise determining at least one of a longitudinal relaxation rate ($R_1$), a transverse relaxation rate ($R_2$), a proton density (PD) for the portion, and a fraction of the partial volume compartment present in the portion.

The fraction discloses to which extent a portion (one or more acquisition voxels) comprises a certain partial volume compartment. For example, to which extent a portion is occupied by a tissue or an aqueous component. Consequently, the fraction can range from 0-100%.

The total acquisition voxel exhibits $R_1$-$R_2$-PD values which reflect the effective, combined relaxation behaviour of all partial volume compartments present within the portion. An MR quantification sequence measures the effective $R_1$-$R_2$-PD values of acquisition voxels in the total imaging portion, which may provide input to the tissue model.

The quantitative magnetic resonance properties may be determined simultaneously in a single magnetic resonance acquisition.

Preferably, multi-parametric quantitative MRI (qMRI) is used where the longitudinal relaxation rate $R_1$, transverse relaxation rate $R_2$ and proton density PD are determined simultaneously in one acquisition. Multi-parametric MR quantification of $R_1$, $R_2$ and PD may be achieved at high resolution within a scan time of 6 to 8 minutes, which would make such an approach attractive for routine clinical use.

The determined non-aqueous tissue volume may be multiplied with a reference factor, thereby obtaining a hydration-corrected tissue volume. The reference factor may be determined based on a number of obtained reference values from a group of reference subjects.

In order to create a measure that is better understandable for a clinician the non-aqueous tissue volume maybe multiplied by a reference factor to estimate the expected 'normal' tissue volume. The reference factor may be derived from a group of reference subjects, where both actual tissue volume (i.e. including intra-tissue aqueous content) and the non-aqueous volume are estimated. The reference subjects may for example be healthy subjects or subjects diagnosed with a certain disease or a certain stage of a disease etc. The ratio actual tissue volume/non-aqueous volume provides a reference factor between the two volumes. Determining the reference factor may also include additional steps such as determining a mean or median value from several values, excluding certain values outside an interval etc. By multiplying the determined non-aqueous tissue volume with the reference factor a measure of the expected hydration-corrected tissue volume in relation to the group of reference subjects is obtained. For example, by multiplying the determined non-aqueous tissue volume from a subject where under- or over-hydration is suspected with a reference factor derived from a group of subjects having a normal tissue hydration, a measure of the expected tissue volume in the absence of possible under- or over-hydration of the tissue is obtained.

The obtained hydration-corrected tissue volume may be presented to a user such as a clinician. Presentation may be performed through a graphical user interface. Other data may be displayed as well such as the volume of the portion, the non-aqueous tissue volume etc. It may be presented as a value, or as an image disclosing a representation of the obtained hydration-corrected tissue volume.

Also, a tissue fraction may be determined by dividing the non-aqueous tissue volume by the total volume of the portion.

The non-aqueous tissue volume may be divided by the total volume of the portion of a subject being examined to obtain a tissue fraction. A value of the tissue fraction may be more convenient for a user to obtain, since it is independent of volume and expresses how much of a portion comprises non-aqueous tissue (ranges from 0-100%).

Also, other relevant fractions may be determined in a corresponding manner. For example, the hydration-corrected tissue volume may be divided by the total volume of the portion to obtain a hydration-corrected tissue fraction. It is also possible to determine an aqueous fraction by dividing the aqueous volume by the total volume of the portion.

As an example, the hydration-corrected brain parenchymal volume (hc-BPV) can be divided by the intracranial volume to obtain the hydration-corrected brain parenchymal fraction (hc-BPF). This measure is independent of the current hydration state of the patient and the possible presence of edema. Therefore, a hydration-corrected tissue fraction is a more robust measure in clinical follow-up of diseases than measurements of uncorrected volumes and fractions.

Any tissue or aqueous fraction may be presented to a user. Presentation may be performed through a graphical user interface. Other data of interest may be displayed as well such as the hydration-corrected tissue volume, total volume of the portion, non-aqueous tissue volume etc. For example, BPF=90.2%, hydration factor 1.02.

According to a second aspect, a device for estimating non-aqueous tissue volume of at least a portion of a subject is provided. The device comprising: a magnetic resonance imaging device for obtaining quantitative magnetic resonance properties of at least a portion of a subject, and a processing unit configured to: obtain quantitative magnetic resonance properties of the portion of the subject, provide the quantitative magnetic resonance properties as input to a tissue model, and determine, based on the tissue model and the quantitative magnetic resonance properties, the non-aqueous tissue volume of the portion.

The processing unit may be further configured to: determine at least one partial volume compartment within the portion, and determine a non-aqueous tissue partial volume present within each partial volume compartment, and determine the non-aqueous tissue volume by adding up all said non-aqueous tissue partial volumes, or determine an aqueous partial volume present within each partial volume compartment, and determine a total aqueous volume by adding up all said aqueous partial volumes, and determine the non-aqueous tissue volume by subtracting the total aqueous volume from a total volume of the portion.

The processing unit, when determining the partial volume compartment, may be further configured to determine at least one of: a longitudinal relaxation rate ($R_1$), a transverse relaxation rate ($R_2$), a proton density (PD) for the portion, and a fraction of the partial volume compartment present in the portion.

The quantitative magnetic resonance properties may be determined simultaneously in a single magnetic resonance acquisition by the magnetic resonance imaging device.

The processing unit may be further configured to multiply the obtained non-aqueous tissue volume with a reference factor, thereby obtaining a hydration-corrected tissue volume. The reference factor may be determined based on a number of obtained reference values from a group of reference subjects.

The processing unit may be further configured to determine a tissue fraction by dividing the non-aqueous tissue volume by the total volume of the portion.

The device may further comprise a presentation unit for presenting information to a user. The presentation unit may comprise a graphical user interface. Also, the presentation may comprise an input device for receiving input from a user.

According to a third aspect, a non-transitory digital storage medium is provided. The non-transitory digital storage medium having stored there on computer program instructions that, when executed by a computer, cause the computer to perform the steps of: obtaining quantitative magnetic resonance properties of the portion of the subject, providing the quantitative magnetic resonance properties as input to a tissue model, determining, based on the tissue model and the quantitative magnetic resonance properties, the non-aqueous tissue volume of the portion.

DETAILED DESCRIPTION

Figure 1:
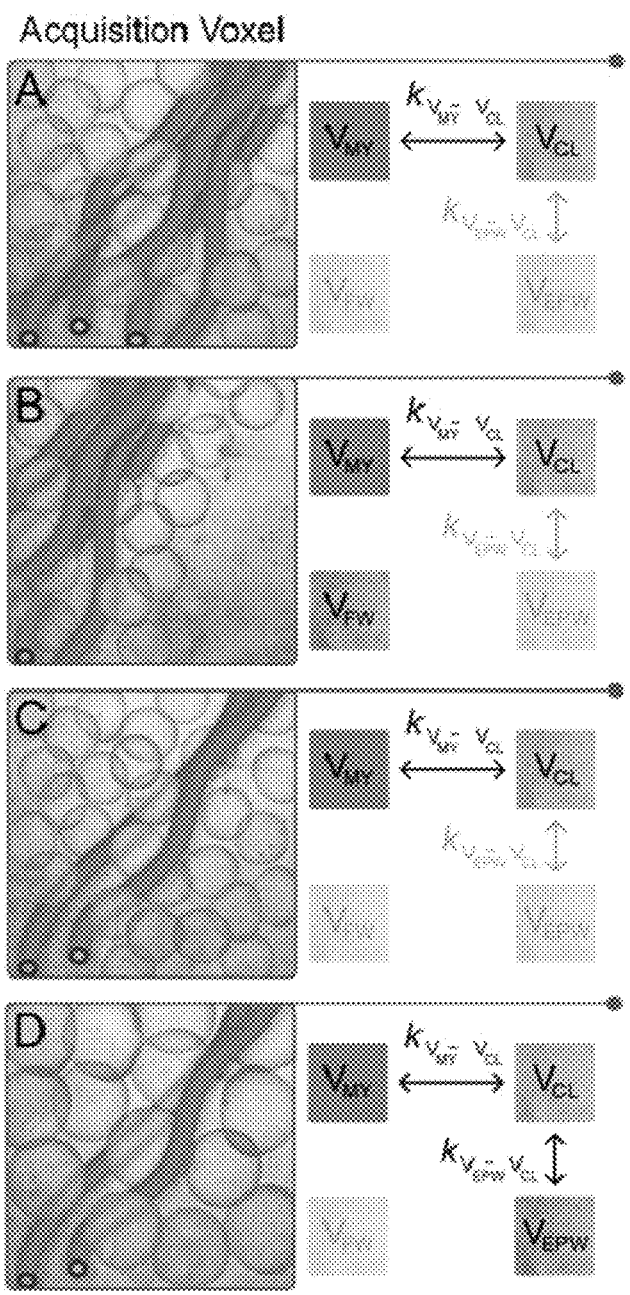
FIG. 1 depicts a proposed compartmental exchange system for modelling brain parenchyma.

FIG. 1 depicts a proposed compartmental exchange system for modelling brain parenchyma. Each MRI acquisition voxel is composed of four partial volume compartments, where each partial volume can range from 0 to 100%, and where the sum is 100%. A compartment is greyed out when its partial volume is equal to zero. The following cases are shown:

Case A: Normal brain parenchyma consists of myelin partial volume $V_{MY}$ and cellular partial volume $V_{CL}$. Between $V_{MY}$ and $V_{CL}$, there is a magnetisation net exchange rate $k_{VMY\text{-}VCL}$.

Case B: At the interface of brain parenchyma with the surrounding bulk CSF, an acquisition voxel contains a mixture of $V_{MY}$ and $V_{CL}$ (i.e. brain parenchyma) and free water partial volume $V_{FW}$. There is no magnetisation exchange between $V_{FW}$ and the other partial volumes.

Case C: In pathological brain parenchyma myelin loss may occur, resulting in a relative decrease in $V_{MY}$. The relative amount of $V_{CL}$ in the acquisition voxel increases to maintain 100% tissue, resulting in a decrease in the total brain volume.

Case D: Alternatively, there can be oedema in pathological brain parenchyma, included in the tissue model by the presence of the non-zero excess parenchymal water partial volume $V_{EPW}$. No distinction can be made between excess parenchymal water and the already present parenchymal water of the $V_{CL}$, making the exchange rate $k_{VEPW\text{-}VCL}$ infinitely high. The combination of $V_{CL}$ and $V_{EPW}$ effectively dilutes the myelin content, resulting in a relative decrease in $V_{MY}$ per acquisition voxel and an increase in the total brain volume.

Figure 2:
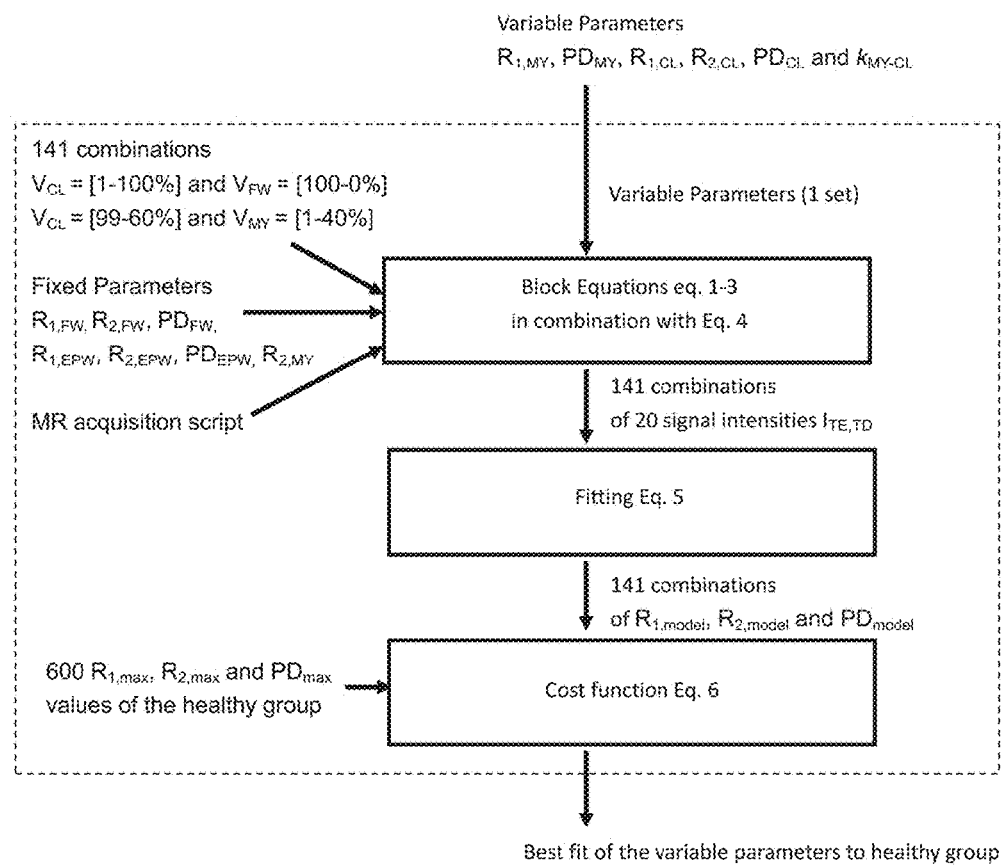
FIG. 2 is a schematic depiction of the procedure to optimize variable parameters.

FIG. 2 is a schematic depiction of the procedure to optimize the variable parameters. One set of variable parameters is chosen and evaluated within the dotted box. Evaluation is performed by running the Bloch equations of the simulated MR acquisition on 141 combinations of $V_{MY}$, $V_{CL}$ and $V_{FW}$. This provides 20 signal intensities at various echo times and saturation delays times. The 20 signal intensities are fitted, resulting in an $R_1$, $R_2$ and PD value of the tissue model. The tissue model values are then compared to the observed $R_1$, $R_2$ and PD values of the healthy group using the maximum values in the 2D histograms. A cost function provides a measure for closeness of the model $R_1$, $R_2$ and PD values to the observed $R_1$, $R_2$ and PD values. The evaluation is performed for many sets of variable parameters, resulting in the best fit.

Figure 3:
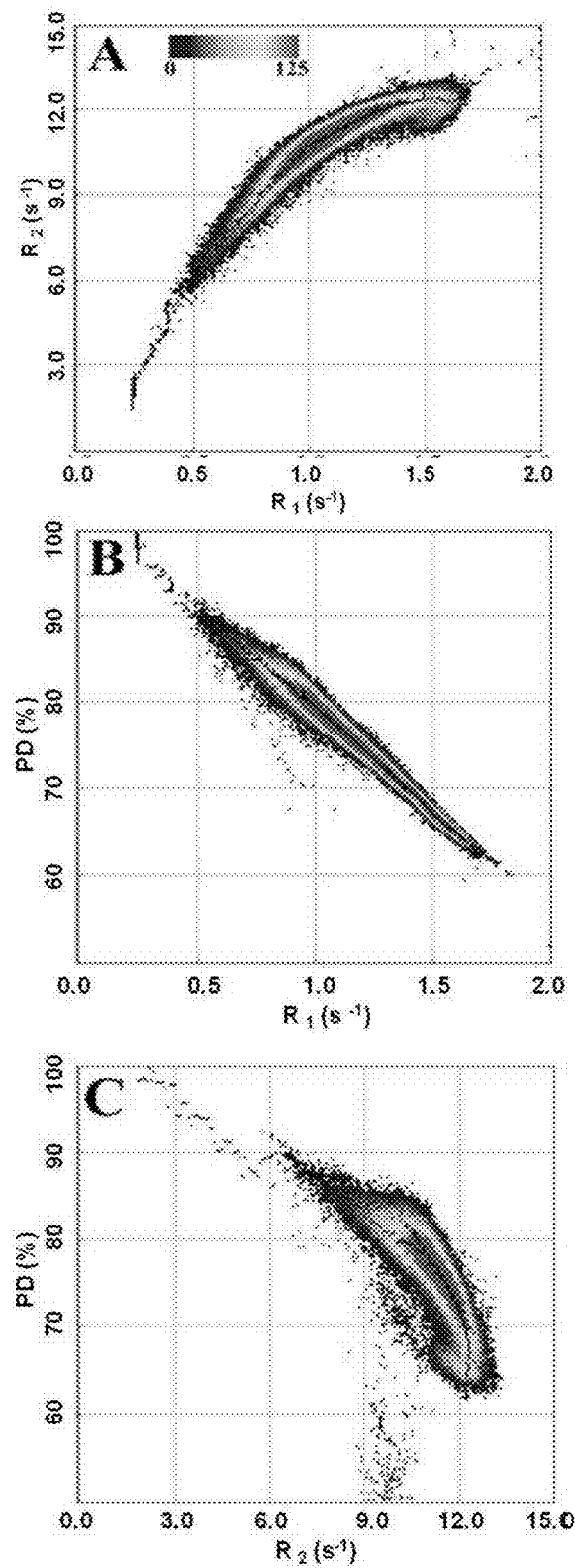
FIG. 3 depicts 2-dimensional histograms of $R_1$, $R_2$ and PD values for spatially normalized brain images of a group of control subjects.

FIG. 3 shows 2D-histograms of $R_1$, $R_2$ and PD values for the spatially normalised brain images of the group of control subjects. The 2D-histograms of $R_1$ and $R_2$, $R_1$ and PD and $R_2$ and PD are shown in A, B and C, respectively. The colour scale indicates the number of voxels for each coordinate. The black dots are placed at the maximum values of the 2D-histograms in each direction.

Figure 4:
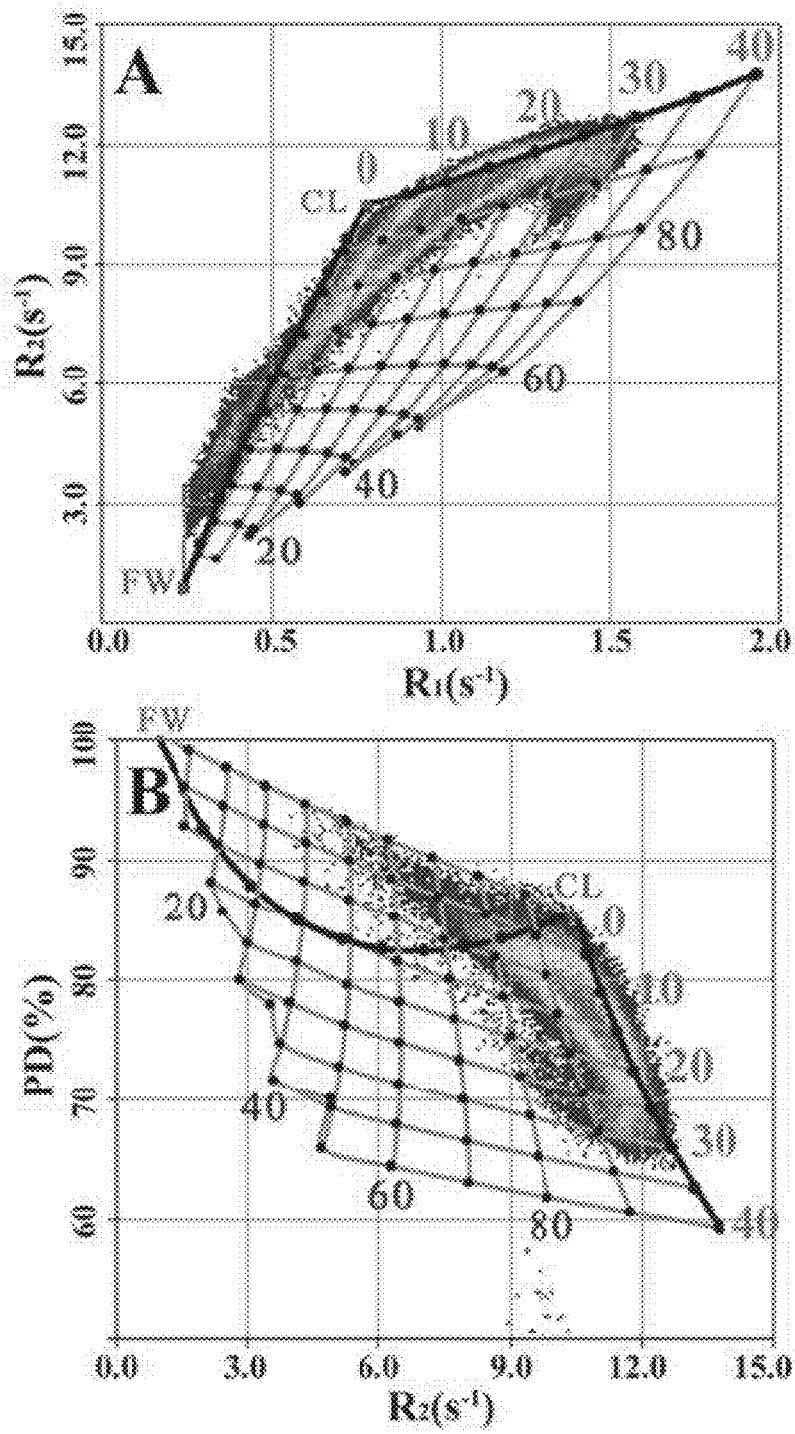
FIG. 4 depicts 2-dimensional histograms of $R_1$, $R_2$ and PD values for spatially normalized brain images of a group of MS patients.

FIG. 4 depicts $R_1$, $R_2$ and PD values for the spatially normalised brain images of the group of MS patients, plotted in the same manner as FIG. 3 for the $R_1$-$R_2$ and $R_2$-PD projections. Additionally, the thick black line indicates the transition from 100% $V_{FW}$ (the red dot at 'FW') to 100% $V_{CL}$ (the red dot at 'CL') until 40% $V_{MY}$, using the tissue model parameter settings for the healthy controls (Table 1). The grid of grey lines indicates the expected changes in $R_1$, $R_2$ and PD values for the pathological brain under myelin loss (FIG. 1, case C) and under the presence of excess parenchymal water (FIG. 1, case D). The cross points of the grid are placed at each 5% change in $V_{MY}$ and each 10% change in $V_{EPW}$. The $V_{MY}$ partial volume is indicated by the grey numbers 0-40%. The $V_{EPW}$ partial volume is indicated by the blue numbers 20-80%.

Figure 5:
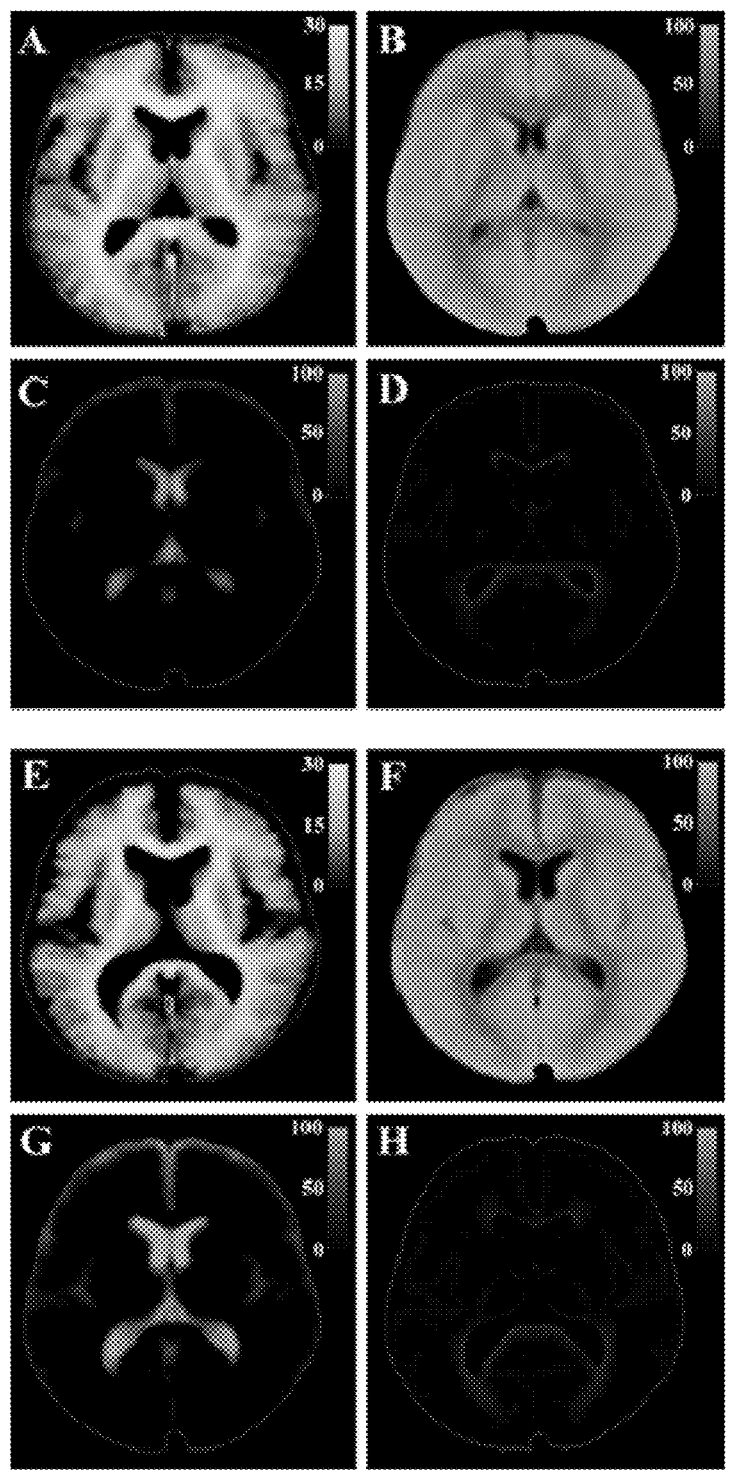
FIG. 5 depicts tissue model calculation of $V_{MY}$, $V_{CL}$, $V_{FW}$ and $V_{EPW}$ of a central slice of the brain of a spatially normalized group of healthy controls and of a spatially normalized group of MS patients.

FIG. 5 is a tissue model calculation of (A) $V_{MY}$, (B) $V_{CL}$, (C) $V_{FW}$ and (D) $V_{EPW}$ of the central slice of the brain of the spatially normalised group of healthy controls and of the spatially normalised group of MS patients (E-H, respectively). The red line indicates the intracranial volume. Note that $V_{MY}$ is scaled to 30%, whereas the other partial volumes are scaled to 100%.

Figure 6:
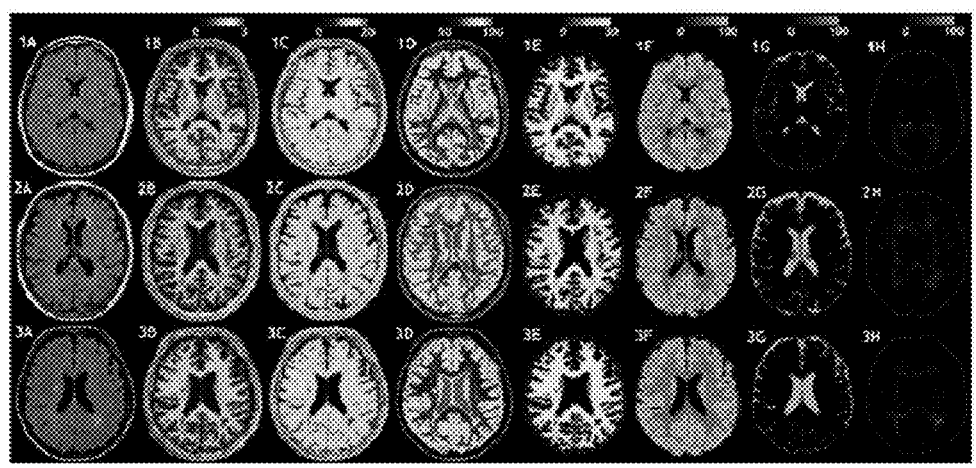
FIG. 6 depicts examples of tissue model calculation on an axial slice of the brain of a healthy subject (row 1), an elderly control subject (row 2) and an MS patient (row 3).

In FIG. 6 examples of the tissue model calculation on an axial slice of the brain is depicted. Row 1: Healthy subject, female 45 years old, row 2: elderly control subject, female 72 years old and row 3: patient, female, 45 years old, diagnosed with secondary progressive MS. (A) A conventional FLAIR image of the same slice is added as a visual reference. (B) The measured $R_1$ relaxation rate is shown on a scale of 0-3 $s^{-1}$, (C) the $R_2$ relaxation rate is shown on a scale of 0-20 $s^{-1}$ and (D) the proton density PD is shown on a scale of 50-100%, where 100% corresponds to pure water at 37° C. (E) Using the $R_1$, $R_2$ and PD values in combination with the look-up grid of FIG. 4 the myelin partial volume $V_{MY}$ was calculated, as shown on a scale of 0-30%, (F) the cellular partial volume $V_{CL}$, (G) free water partial volume $V_{FW}$ and (H) excess parenchymal water partial volume $V_{EPW}$ were all calculated all on a scale 0-100%. The red intracranial cavity outline is displayed in all tissue images for visual guidance.

Figure 7:
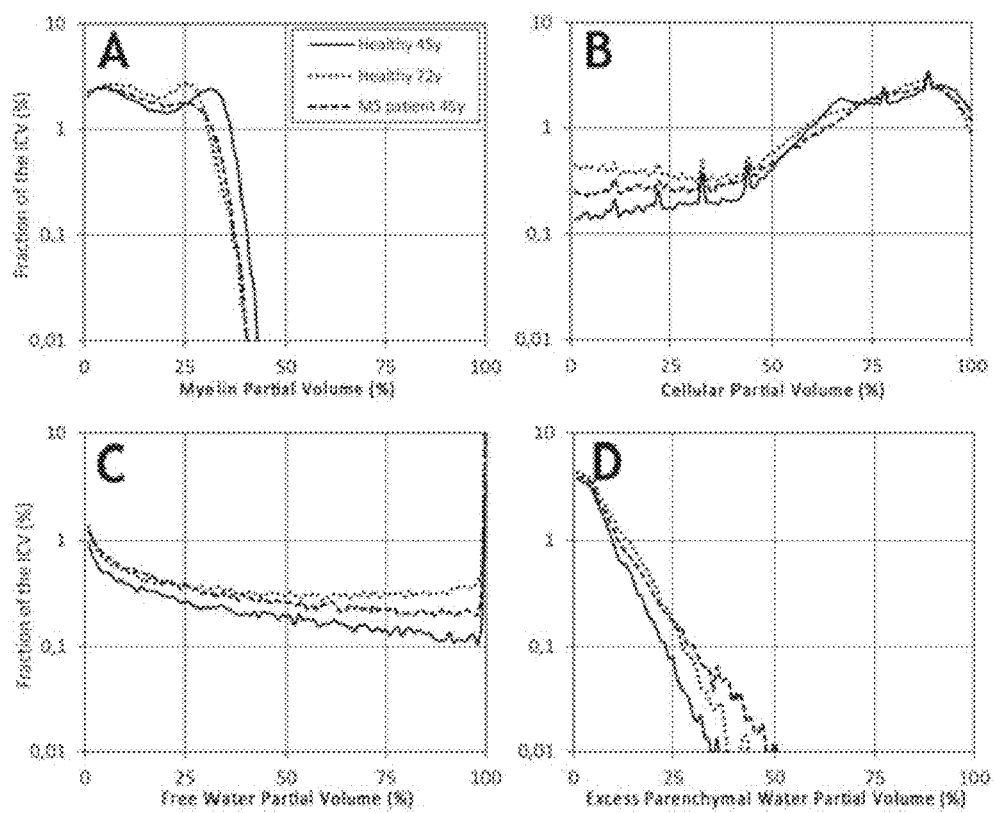
FIG. 7 depicts histograms of $V_{MY}$, $V_{CL}$, $V_{FW}$ and $V_{EPW}$ partial volume distributions of the control subject, elderly control subject and MS patient in FIG. 6.

FIG. 7 shows histograms of the (A) $V_{MY}$, (B) $V_{CL}$, (C) $V_{FW}$ and (D) $V_{EPW}$ partial volume distributions of the control subject (solid line), elderly control subject (dotted line) and MS patient (dashed line) from FIG. 6. The x-axis was divided into 100 bins of 1% partial volume over the range 0-100%. The scaling on the y-axis is logarithmic, as a percentage of the ICV.

Figure 8:
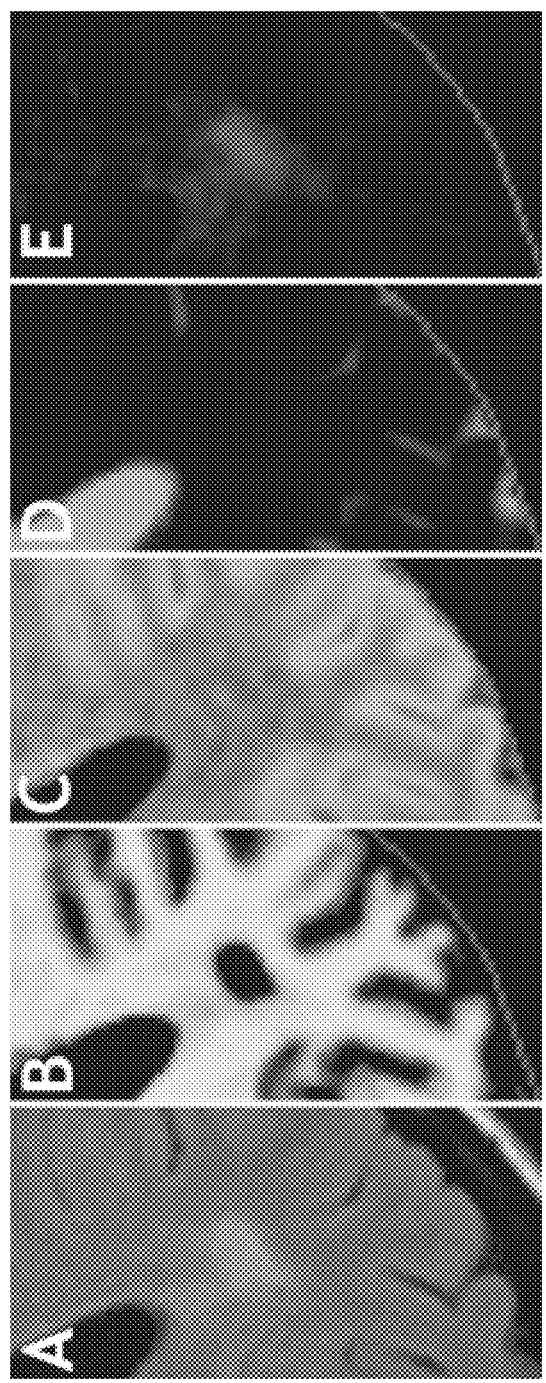
FIG. 8 shows zoomed parts of an MS lesion of the same MS patient as in FIGS. 6 and 7.

In FIG. 8 there is a zoomed part on an MS lesion of the patient in FIG. 6, row 3. Shown are (A) the conventional FLAIR image, (B) myelin partial volume $V_{MY}$, (C) cellular partial volume $V_{CL}$, (D) free water partial volume $V_{FW}$ and (E) excess parenchymal water partial volume $V_{EPW}$. Color scaling is identical to FIG. 6.

Figure 9:
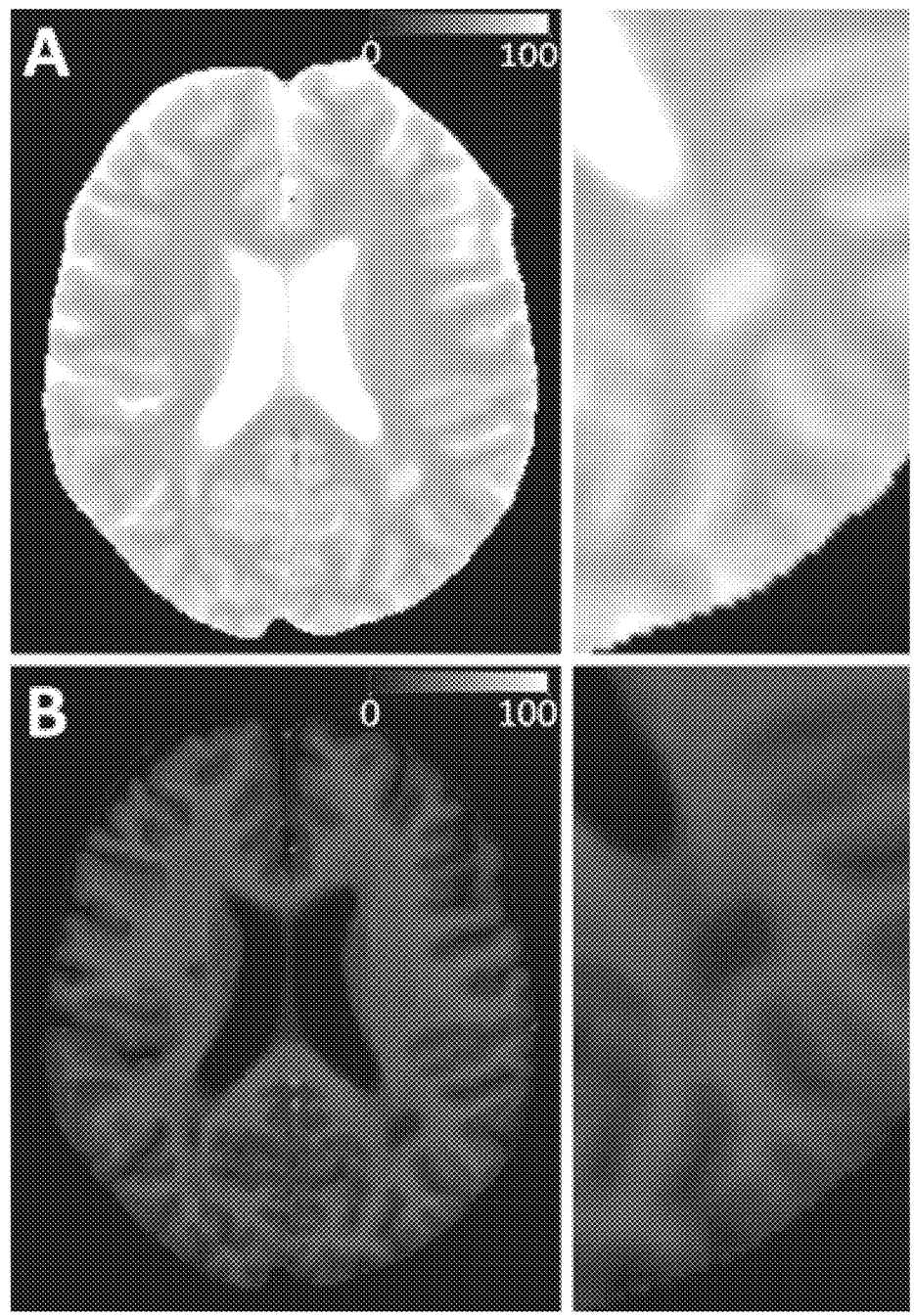
FIG. 9 depicts an example of an axial slice of the brain with calculated total aqueous content (A) and total non-aqueous content (B) of the same MS patient as in FIG. 6-8.

FIG. 9 depicts calculated total aqueous content (A), corresponding to the sum of myelin water, cellular water, free water and excess parenchymal water, and the remaining, total non-aqueous content (B) of the 45y-MS patient. The same slice and zoomed part are displayed as in FIGS. 6 and 8.

Figure 10:
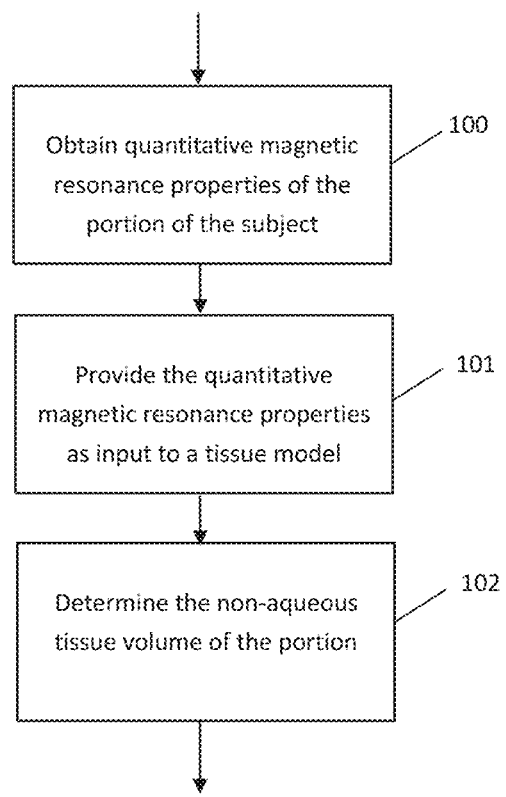
FIG. 10 is a schematic representation of a method according to an embodiment of the present application.

FIG. 10 is a schematic representation of a method for estimating non-aqueous tissue volume, the method comprising steps 100-104.

Figure 11:
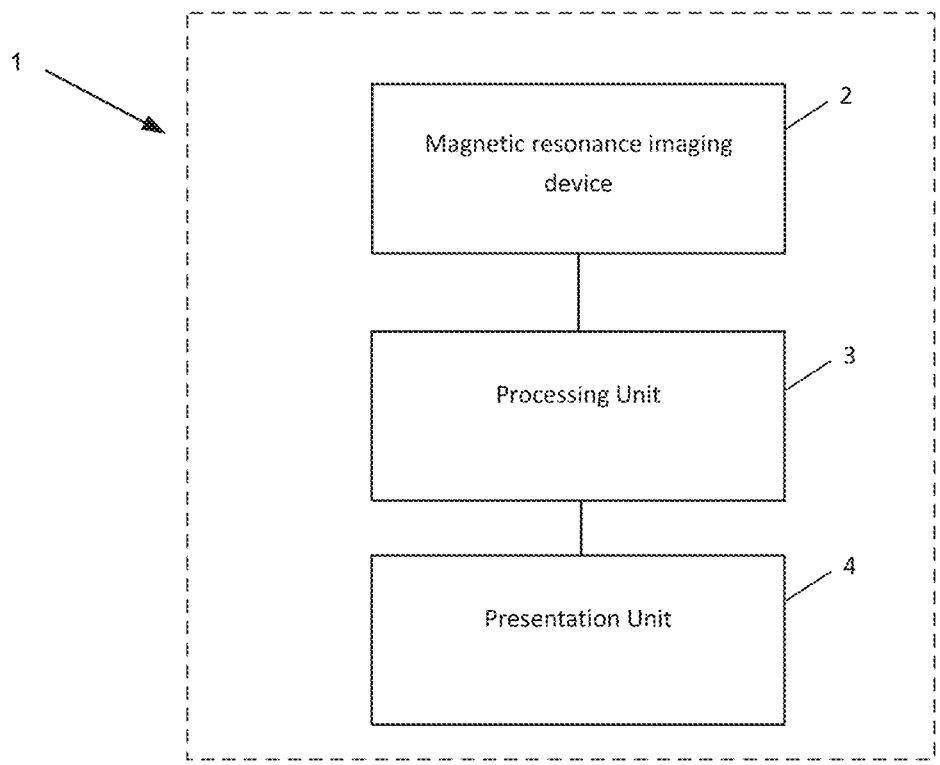
FIG. 11 is a schematic representation of a device according to an embodiment of the present application.

FIG. 11 shows a schematic representation of a device 1. The device 1 comprises a magnetic resonance imaging device 2 and a processing unit 3.

Figure 12:
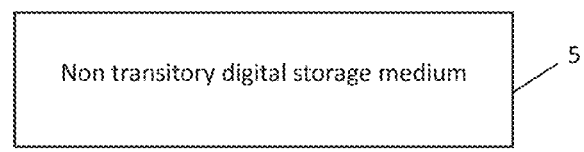
FIG. 12 is a schematic representation of a non-transitory digital storage medium according to an embodiment of the present application.

FIG. 12 schematically depicts a non-transitory digital storage medium 4 having stored there on computer program instructions that may be executed by a computer.

In Magnetic Resonance Imaging (MRI) there are three main physical properties that have an effect on signal intensity in the MR images: The longitudinal $R_1$ relaxation rate, the transverse $R_2$ relaxation rate and the proton density PD. In order to understand MRI contrast, it is relevant to have some understanding of the time constants involved in relaxation processes that establish equilibrium following RF excitation. As the excited protons relax and realign, they emit energy at rates which are recorded to provide information about their environment. The realignment of proton spins with the magnetic field is termed longitudinal relaxation and the time (typically about 1 sec) required for a certain percentage of the tissue nuclei to realign is termed "Time 1" or $T_1$. $T_2$-weighted imaging relies upon local dephasing of spins following the application of the transverse energy pulse; the transverse relaxation time (typically <100 ms for tissue) is termed "Time 2" or $T_2$. These relaxation times are also expressed as relaxation rates $R_1$ (=1/$T_1$) and $R_2$ (=1/$T_2$). The total signal depends on the number of protons, or proton density PD. On the scanner console all available parameters, such as echo time $T_E$, repetition time $T_R$, flip angle α and the application of preparation pulses (and many more), are set to certain values. Each specific set of parameters generates a particular signal intensity in the resulting images depending on the characteristics of the measured tissue.

The three properties longitudinal relaxation rate $R_1$, transverse relaxation rate $R_2$ and proton density PD can be measured on with quantitative MRI. In contrast to conventional MR imaging, which results in qualitative images with a relative image intensity scale, a quantitative MRI scan results in the measurement of physical properties such as $R_1$, $R_2$ and PD on an absolute scale. These values are independent of scanner settings and hence directly reflect the underlying tissue. Thus, each tissue type has its own characteristic combination of $R_1$, $R_2$ and PD. For example the mean values for white matter in the brain are approximately ($R_1$, $R_2$, PD)=(1.7 s−1, 14 s−1, 64%), for grey matter (1.0 s−1, 12 s−1, 85%) and for cerebrospinal fluid (0.24 s−1, 1.5 s−1, 100%) (see e.g. Warntjes et al. Rapid Magnetic Resonance Quantification on the Brain: Optimization for Clinical Usage Magn Reson Med 2008; 60:320-329).

Including noise of the measurement and partial volume effects, an area in the multi-parametric $R_1$-$R_2$-PD space can be specified to contain brain tissue and cerebrospinal fluid CSF. These values differ from for example muscle or fat. Alternatively, $R_1$, $R_2$ and PD can be used to classify the intracranial volume into a myelin partial volume, a cellular partial volume, an excess parenchymal water partial volume and a free water partial volume (see Warntjes et al. Modeling the Presence of Myelin and Edema in the Brain Based on Multi-Parametric Quantitative MRI, Frontiers in Neurology 2016, doi 10.3389). The sum of myelin partial volume and cellular partial volume can be regarded as normal brain tissue, the excess parenchymal water partial volume as edema and free water partial volume corresponds to cerebrospinal fluid CSF. Since all classified tissue has a certain PD value, corresponding to the water content (PD=100% is pure water), the tissue's non-aqueous component can be calculated as 1−PD. The sum of all non-aqueous components provides the total non-aqueous content of the tissue.

In order to create a measure that is better understandable for a clinician the non-aqueous (dry mass) volume can be multiplied by a reference factor to estimate the expected 'normal' tissue volume with this measured non-aqueous content. The reference factor can be derived from a group of healthy subjects, where both actual tissue volume and the non-aqueous volume are estimated. The ratio actual/non-aqueous provides the normal, reference factor between the two volumes. In this way, a measure of the expected tissue volume in the absence of possible under- or over-hydration of this tissue is provided. The hydration-corrected tissue volume may be divided by the total volume of the portion of a subject being examined to obtain a hydration-corrected tissue fraction. For example, the hydration-corrected brain parenchymal volume (hc-BPV) can be divided by the intracranial volume to obtain the hydration-corrected brain parenchymal fraction (hc-BPF). This measure is independent of the current hydration state of the patient and the possible presence of edema. Therefore it is expected that the hc-BPV and hc-BPF are more robust measures in clinical follow-up of neuro-degenerative diseases than a measurement of uncorrected BPV and BPF. Alternatively, the hydration correction factor can be given, calculated as the hc-BPF divided by the actual BPF. In that case, the measured BPF can still be displayed to the clinician, together with the information in hydration state as a relative measure. Similarly, hydration-corrected muscle volume, hydration-corrected muscle mass and hydration-corrected muscle fraction are expected to be more robust measures for follow-up of muscle-degenerative diseases than uncorrected muscle volume, muscle mass or muscle fraction. Correspondingly, hydration-correction of other types of soft tissue such as tissue of internal organs, skin, fat and so on may also be of interest for monitoring a variety of diseases.

A description of how to estimate the non-aqueous tissue volume in the brain based on Magnetic Resonance Imaging follows below. However, as mentioned above the subject-matter disclosed herein may also be used when estimating non-aqueous volume of other kinds of soft tissue such as tissue of muscles, internal organs and so on. Rather than partial volume compartments such as myelin, cellular, excess parenchymal water and free water for brain, other compartments may be necessary for calculating the non-aqueous tissue volume outside the brain, such as blood vessel partial volume, fat partial volume, bone partial volume or tendon partial volume.

Myelin is crucial for efficient signal transmission over long ranges in the nervous system because it increases the speed at which the impulses propagate along the axons. Axons are coated piecewise by multiple layers of phospholipid membranes ('sheaths') with embedded proteins produced by oligodendrocytes and Schwann cells in the central and peripheral nervous systems, respectively. Degradation of myelin impairs the signal transmission, and the nerve may eventually wither, leading to brain atrophy and brain dysfunction. Knowledge of myelin content supports the investigation of early brain development. Accurate myelin measurements are valuable in studies of neurodegenerative diseases, such as multiple sclerosis (MS) and dementia. Thus, measurements and monitoring of myelin content would provide information for the diagnosis and prognosis in patients with suspected myelin degradation.

One established MRI method for myelin detection is based on the measurement of the multi-exponential transverse $T_2$ relaxation time using a Carr-Purcell-Meiboom-Gill (CPMG) sequence [8-10]. The short-time component of the observed $T_2$ relaxation represents the presence of water trapped between the myelin sheaths, termed myelin water (MyW), whereas the medium-time $T_2$ relaxation component is attributed to the intra- and extracellular water. Commonly, the myelin water fraction (MWF), corresponding to the ratio of both components, is calculated. The proportionality of MWF with the myelin content has been verified in vitro and by histopathology. More recently, an alternative approach called mcDESPOT was developed. This method consists of a combination of spoiled gradient echo (SPGR) and balanced steady-state free precession (bSSFP) acquisitions at multiple flip angles, resulting in the measurement of myelin water and intra- and extracellular water pools. In particular, the mcDESPOT method has been applied to myelin development in children.

Limitations of the two described methods are mainly practical. Due to the very short myelin $T_2$ relaxation time (10-15 ms), the multi-exponent $T_2$ measurement mainly depends on the amplitude of the first echo signal, and mcDESPOT is highly sensitive to the accuracy of the applied flip angle, making the measurements demanding in terms of both SNR and time as well as highly dependent on corrections for $B_1$ field and RF pulse profile effects. The underlying models of both approaches are considerably different, resulting in widespread estimations of the myelin content.

In the tissue model, estimation of the presence of myelin and oedema in the brain is based on multi-parametric quantitative MRI (qMRI), where the longitudinal relaxation rate $R_1$, transverse relaxation rate $R_2$ and proton density PD are determined simultaneously in one acquisition. It was previously reported that pathological processes such as axonal damage, gliosis, inflammation and oedema are related to changes in the values of $R_1$, $R_2$ and PD. Currently, multi-parametric MR quantification of $R_1$, $R_2$ and PD can be achieved at high resolution within a 6 to 8 minute scan time, which would make such an approach attractive for routine clinical use.

The Relaxation Model

A tissue model for observed $R_1$, $R_2$ and PD values of the brain is visualised in FIG. 1: Each MRI acquisition voxel is composed of four partial volume compartments: the myelin partial volume $V_{MY}$, cellular partial volume $V_{CL}$, free water partial volume $V_{FW}$ and excess parenchymal water partial volume $V_{EPW}$. The content in each partial volume compartment can range from 0 to 100%, where the sum of the four compartments is 100%. Each partial volume compartment has its own relaxation properties ($R_{1,MY}$, $R_{2,MY}$, $PD_{MY}$, $R_{1,CL}$, $R_{2,CL}$, $PD_{CL}$, $R_{1,FW}$, $R_{2,FW}$, $PD_{FW}$, $R_{1,EPW}$, $R_{2,EPW}$, $PD_{EPW}$), without further detailed knowledge of the multitude of interacting pools within each of the compartments. Using this approach, each partial volume compartment can be described by its $R_1$-$R_2$-PD values, its fraction of the acquisition voxel and the magnetisation exchange with other partial volume compartments. The total acquisition voxel exhibits $R_1$-$R_2$-PD values which reflect the effective, combined relaxation behaviour of all four compartments. An MR quantification sequence measures the effective $R_1$-$R_2$-PD values of acquisition voxels in the total imaging volume, which can provide input to the tissue model.

In general, relaxation times may be expressed as being fast (around 0-50 ms), intermediate (around 50-500 ms) or long (around 500 ms or longer).

The $V_{MY}$ contains the thin layers of myelin water and myelin sheets that are closely packed around the axons. The close proximity of myelin water to the surrounding structure results in a very fast relaxation of this compartment. The $V_{CL}$ consists of intra- and extracellular (interstitial) water, axonal water and all cellular macromolecules, not being related to myelin. The presence of the macromolecules results in a medium-time relaxation of $V_{CL}$, which is longer than $V_{MY}$, but shorter than $V_{FW}$. Between $V_{MY}$ and $V_{CL}$ there is a magnetisation exchange rate $k_{VMY-VCL}$. In the tissue model, acquisition voxels in the normal brain parenchyma contain a mixture of $V_{MY}$ and $V_{CL}$, where voxels in GM have a low $V_{MY}$ and voxels in WM have a high $V_{MY}$ (see FIG. 1, case A). The two compartments $V_{MY}$ and $V_{CL}$ are an approximation of the 4-pool model, where $V_{MY}$ contains myelin water and myelin semi-solids and $V_{CL}$ contains intracellular and extracellular water and non-myelin semi-solids pools, albeit with less degrees of freedom.

The brain is surrounded by cerebrospinal fluid (CSF), making it necessary to add a free water partial volume $V_{FW}$ to the tissue model. Because bulk CSF is physically separated from the brain parenchyma except for the interface, there is no magnetisation exchange between $V_{FW}$ and any other compartment (i.e. 'free'). Hence, at the border of the brain, acquisition voxels contain a mixture of $V_{MY}$ and $V_{CL}$ (brain parenchyma) and $V_{FW}$ (CSF), see FIG. 1, case B.

In the pathological brain two distinct processes are modelled: compared with the normal brain, there can be myelin loss, resulting in a relative decrease in $V_{MY}$. To maintain 100% tissue, the relative amount of $V_{CL}$ in an acquisition voxel will increase. Therefore the loss of myelin results in a compaction of the brain and thus a decrease in the total brain volume (FIG. 1, case C). The second process is the occurrence of oedema, modelled as the presence of excess parenchymal water partial volume $V_{EPW}$, which adds water to $V_{CL}$. No distinction can be made between excess parenchymal water and the already present parenchymal water of $V_{CL}$ and therefore, the exchange rate $k_{VEPW-VCL}$ is infinitely high. Modelling two separate partial volume compartments with an infinite exchange is a mathematical approach to acquire knowledge on the degree of oedema without knowledge of the exact internal composition of $V_{CL}$. The cellular swelling due to a non-zero $V_{EPW}$ effectively dilutes the myelin present in the acquisition voxel, resulting in a relative decrease in $V_{MY}$. In this case, the total brain volume increases (FIG. 1, case D).

Bloch Simulation

A numerical simulation of coupled Bloch equations of the four partial volume compartments was performed using 150 identical magnetisation elements i, spread equidistantly over a distance of 15 mm in the acquisition slice direction, where each element had a distance from the centre of the slice. Each of the 150 elements consisted of the same partial volume distribution of interacting $V_{MY}$, $V_{CL}$, $V_{FW}$ and $V_{EPW}$ with normalised magnetisation vectors $M_{MY}$, $M_{CL}$, $M_{FW}$ and $_{MEPW}$, respectively. The evolution of each magnetisation $M_i = [M_x M_y M_z]_i^T$ was calculated in small time steps t, where each sequential magnetisation $M_{i, n+1}$ of each element i was calculated from the original magnetisation $M_{i, n}$ using:

$$M_{i,n+1} = R_{RF} * R_{GR} * R_{R1} * R_{R2} * M_{i,n} \qquad [1]$$

$R_{RF}$ is the rotation matrix for the applied slice-selective RF pulses. The envelope of the RF pulses was approximated by a series of block pulses with constant amplitudes over the time interval t. The rotation flip angle $\alpha$, achieved in time t over the x- or y-axis, is equal to $2\pi\gamma B_1 t$, where $B_1$ is the amplitude of the RF pulse at that particular time interval, and $\gamma$ is the gyromagnetic ratio. $R_{GR}$ is the rotation matrix for the applied slice-selective gradients. The rotation flip angle $\omega$, achieved in time t over the z-axis, is equal to $2\pi\gamma G d_i t$, where G is the gradient strength and $d_i$ is the distance from the centre of the slice.

$R_{R1}$ is the relaxation matrix for the elements for the longitudinal relaxation rate $R_1$. $R_{R1}$ only acts on the $M_z$ component of each $M_i$ according to:

$$\begin{bmatrix} M_{z,MY} \\ M_{z,CL} \\ M_{z,FW} \\ M_{z,EPW} \end{bmatrix}_{i,n+1} = \begin{bmatrix} E_{1,MY} - S_{MY}(1-K_{MC}) & S_{MY}(1-K_{MC}) & 0 & 0 \\ S_{CLa}(1-K_{MC}) & E_{1,CL} - S_{CLa}(1-K_{MC}) - S_{CLb} & 0 & S_{CLb} \\ 0 & 0 & E_{1,FW} & 0 \\ 0 & S_{EPW} & 0 & E_{1,EPW} - S_{EPW} \end{bmatrix} * \begin{bmatrix} M_{z,MY} \\ M_{z,CL} \\ M_{z,FW} \\ M_{z,EPW} \end{bmatrix}_{i,n} + \begin{bmatrix} 1-E_{1,MY} \\ 1-E_{1,CL} \\ 1-E_{1,FW} \\ 1-E_{1,EPW} \end{bmatrix} \qquad [2]$$

where $E_{1,MY} = \exp(-tR_{1,MY})$, $E_{1,CL} = \exp(-tR_{1,CL})$, $E_{1,FW} = \exp(-tR_{1,FW})$, $E_{1,EPW} = \exp(-tR_{1,EPW})$ and $K_{MC} = \exp(-tk_{MY-CL})$. The exchange rate $K_{MC}$ is the combined forward and backward exchange rate between $V_{MY}$ and $V_{CL}$. The exchange rate between $V_{EPW}$ and $V_{CL}$ is infinitely high. The scaling factors $S_{MY} = V_{CL} * PD_{CL}/(V_{MY} * PD_{MY} + V_{CL} * PD_{CL})$, $S_{CLa} = V_{MY} * PD_{MY}/(V_{MY} * PD_{MY} + V_{CL} * PD_{CL})$, $S_{CLb} = V_{EPW} * PD_{EPW}/(V_{EPW} * PD_{EPW} + V_{CL} * PD_{CL})$ and $S_{EPW} = V_{CL} * PD_{CL}/(V_{EPW} * PD_{EPW} + V_{CL} * PD_{CL})$ are required to take the relative volumes of PD in each compartment into account.

$R_{R2}$ is the relaxation matrix for the elements for the transverse relaxation rate $R_2$. $R_{R2}$ only acts on the $M_{xy}$ component of each $M_i$ according to:

$$\begin{bmatrix} M_{xy,MY} \\ M_{xy,CL} \\ M_{xy,FW} \\ M_{xy,EPW} \end{bmatrix}_{i,n+1} = \begin{bmatrix} E_{2,MY} - S_{MY}(1-K_{MC}) & S_{MY}(1-K_{MC}) & 0 & 0 \\ S_{CLa}(1-K_{MC}) & E_{2,CL} - S_{CLa}(1-K_{MC}) - S_{CLb} & 0 & S_{CLb} \\ 0 & 0 & E_{2,FW} & 0 \\ 0 & S_{EPW} & 0 & E_{2,EPW} - S_{EPW} \end{bmatrix} * \begin{bmatrix} M_{xy,MY} \\ M_{xy,CL} \\ M_{xy,FW} \\ M_{xy,EPW} \end{bmatrix}_{i,n} \qquad [3]$$

where $E_{2,MY} = \exp(-tR_{2,MY})$, $E_{2,CL} = \exp(-tR_{2,CL})$, $E_{2,FW} = \exp(-tR_{2,FW})$, $E_{2,EPW} = \exp(-tR_{2,EPW})$.

MR Quantification Sequence

The presented Bloch equations form a general description of the magnetisation evolution for each acquisition voxel and only have meaning when applied to an actual MRI sequence. The specifics of this MRI sequence, with the applied RF pulses, gradients and timings, dictate the observable signal behaviour. The MRI quantification method employed was a multi-echo, multi-delay saturation recovery spin echo sequence (QRAPMASTER). It was a multi-slice sequence where slice-selective saturation pulses were interleaved with a Carr-Purcell-Meiboom-Gill (CPMG) acquisition of 5 echoes at 14-ms multiples. The saturation pulse acted on slice n, whereas the subsequent acquisition acted on slice m. By a fixed shift between slices n and m an effective delay time TD was created between the saturation and acquisition of each particular slice. The sequence was repeated 4 times where the shift between n and m, and hence the saturation delay, was changed. The result of the sequence was a matrix of 20 images at 5 different echo times TE and at 4 different saturation delay times TD. The applied slice-selective RF pulse profiles and amplitudes, gradient strengths and timings were extracted from the scanner. The repetition time TR was 2950 ms with 30 slices of 4-mm thickness with an in-plane resolution of 1 mm. The saturation pulse had a flip angle of 120 degrees over the x-axis followed by a delay of 100, 400, 1380 and 2860 ms, corresponding to a shift between n and m of 1, 4, 14 and 29 slices, respectively. The excitation pulse had a flip angle of 90 degrees over the x-axis, followed by refocusing pulses of 180 degrees over the y-axis. The refocusing pulses were straddled by spoiler gradients. The scan time was 8:21 minutes on a Philips Achieva 1.5T (Philips Healthcare, Best, The Netherlands).

Application of the Bloch Simulation on the Quantification Sequence

The RF pulses, gradients and timings of the quantification sequence were implemented as a script into the tissue model calculations. The product of all matrices in Eq. 1 does not commute (AB BA), and therefore Eq. 1 is only valid if time-steps are chosen such that the relaxation rates cause a near-zero change of magnetization per time step. Typical relaxation in the brain occurs in the order of ms. Therefore we choose time steps t of 1 µs, which is three orders of magnitude smaller, but still results in a reasonable calculation time. The observable signal intensity I at each combination of TE and TD was calculated as the product of the total proton density for each partial volume (V*PD) and the xy-component of the magnetisation $M_i$ of these spins, summed over all elements i:

$$I_{TE,TD} = \Sigma_i (V_{MY}*PD_{MY}*M_{xy,MY} + V_{CL}*PD_{CL}*M_{xy,CL} + V_{FW}*PD_{FW}*M_{xy,FW} + V_{EPW}*PD_{EPW}*M_{xy,EPW})_{TE,TD} \quad [4]$$

In this way the Block simulation also produced 20 images with different TE and TD, identical to the in vivo quantification sequence.

Subjects

MR quantification was performed on two groups of subjects, one with patients diagnosed with Clinically Definite Multiple Sclerosis (5 males and females; mean age of 47±12 years). The mean Extended Disability Status Scale (EDSS) of the MS group was 3.6±2.2, and the mean disease duration was 15±10 years. The second group consisted of age- and gender-matched healthy controls (5 males and 15 females; mean age of 47±11 years). Three female participants were used as individual examples: one healthy subject of years old, one healthy subject of 72 years old, and a secondary progressive MS patient of 45 years old (EDSS of 3.5; disease duration of 17 years). The study was approved by the regional ethical review board and written informed consent was obtained from all participants (full name of the board: 'Regionala etikprövningsnämnden i Linköping'; registered under number Dnr. M88-07).

Image Post-Processing $R_1$, $R_2$ and PD maps were retrieved from both the simulated and in vivo acquired images using SyMRI 7.0 (SyntheticMR, Linköping, Sweden). In summary, a least squares fit was performed as a function of the different TE and TD times according to:

$$I_{TE,TD} = A \cdot PD \cdot \exp(-R_2 TE) \cdot \frac{1 - [1 - \cos(B_1\theta)] \cdot \exp(-R_1 TD) - \cos(B_1\theta) \cdot \exp(-R_1 TR)}{1 - \cos(B_1\alpha) \cdot \cos(B_1\theta) \cdot \exp(-R_1 TR)} \quad [5]$$

where a is the excitation flip angle, θ is the saturation flip angle and $B_1$ is the amplitude of the $B_1$ field. A is an overall scaling factor that considers the coil sensitivity, RF chain amplification and voxel volume. This equation explicitly has two mono-exponential functions, in $R_1$ and $R_2$, and hence it will reflect the dominant component of the relaxation behaviour.

For spatial normalisation of the in vivo brain data, the $R_1$, $R_2$ and PD maps were used to synthesize a stack of $T_2$-weighted images with TE=100 ms and TR=4500 ms. The synthetic $T_2$-weighted images were smoothed with an 8-mm Gaussian kernel and used as source images to calculate the transformation matrix to a standard stereotactic space in Montreal Neurological Institute (MNI) coordinates. The images were then transformed to match the size and position of a standard template using a 12-parameter (translation, rotation, shear, zoom) affine regularisation and non-linear deformations by a linear combination of three-dimensional discrete cosine basis functions. The same transformation matrix was then applied to the $R_1$, $R_2$ and PD maps. The resulting data was re-gridded to 2×2×2 mm³ to obtain an isotropic dataset. All of the subjects were averaged to obtain the mean $R_1$-$R_2$-PD values of the MS and control group. Finally, the mean $R_1$, $R_2$ and PD values were used as coordinates in a $R_1$-$R_2$-PD multi-parametric space. The 2D histograms of the entire brain were created with 200 bins for $R_1$ on a scale of 0-2 s$^{-1}$, 200 bins for $R_2$ on a scale of 0-15 s$^{-1}$ and 200 bins for PD on a scale of 50-100%.

Determining the Model Parameters

The procedure to determine the tissue model parameters is schematically depicted in FIG. 2. In the tissue model, the relaxation parameters for water, both for $V_{FW}$ and $V_{EPW}$, were fixed to literature values for CSF at $R_1$=0.24 s$^{-1}$, $R_2$=0.87 s$^{-1}$ and PD=100%. Additionally, the $R_2$ relaxation for $V_{MY}$ was fixed to a reported value, at $R_{2,MY}$=77 s$^{-1}$ (corresponding to $T_{2,MY}$=13 ms). Therefore, only six remaining tissue model parameters, $R_{1,MY}$, $PD_{MY}$, $R_{1,CL}$, $R_{2,CL}$, $PD_{CL}$ and $k_{MY-CL}$, were allowed to vary.

The six model parameters were given a random value under the restriction that $R_{1,FW} < R_{1,CL} < R_{1,MY}$ and $R_{2,FW} < R_{2,CL} < R_{2,MY}$. For each set of variable parameters the magnetisation evolution was calculated for all combinations of $V_{MY}$ and $V_{CL}$ and for all combinations of $V_{CL}$ and $V_{FW}$, using steps of 1% partial volume. Since the maximum amount is 100%, a setting of for example 20% $V_{FW}$ requires a setting of 80% $V_{CL}$, hence producing 101 combinations of $V_{FW}$ and $V_{CL}$. $V_{MY}$ was restricted to a maximum of 40%, since no higher values were expected to occur in the brain and we wanted to avoid values that could not be evaluated. This produced 40 combinations of $V_{MY}$ and $V_{CL}$, making a total of 141 combinations. The magnetisation evolution was calculated using Eqs. 1-3, resulting in the signal intensities $I_{TE,TD}$ at 5 different echo times TE and 4 different saturation delay times TD for each partial volume combination (Eq. 4). The sets of 20 $I_{TE,TD}$ values were then fitted using Eq. 5, resulting in 141 $R_{1,model}$, $R_{2,model}$ and $PD_{model}$ values for each specific set of variable parameters.

To evaluate how close these 141 $R_1$-$R_2$-PD values mimicked the observed data structure in the 2D histograms of the healthy control group, the maximum values in the histogram for each bin in $R_1$ were determined, and the corresponding $R_2$ and PD values were recorded. This procedure was repeated for $R_2$ and PD. Because the 2D histograms had 200×200 bins, this procedure provided 600 $R_{1,max}$, $R_{2,max}$ and $PD_{max}$ values to define the characteristic data structure of the healthy group. From these 600 combinations 141 were selected that were closest to the 141 model combinations.

Finally, a cost function was set up to evaluate the difference between the $R_{1,model}$, $R_{2,model}$ and $PD_{model}$ values for each parameter setting with the selected $R_{1,max}$, $R_{2,max}$ and $PD_{max}$ values of the 2D histograms of the in vivo spatially normalised data:

$$f_{cost} = \frac{1}{n}\sum \left[\left(\frac{R_{2,model}-R_{2,max}}{\sigma(R_2)}\right)^2 + \left(\frac{PD_{model}-PD_{max}}{\sigma(PD)}\right)^2\right]_{R_1} + \left[\left(\frac{R_{1,model}-R_{1,max}}{\sigma(R_1)}\right)^2 + \left(\frac{PD_{model}-PD_{max}}{\sigma(PD)}\right)^2\right]_{R_2} + \left[\left(\frac{R_{1,model}-R_{1,max}}{\sigma(R_1)}\right)^2 + \left(\frac{PD_{2,model}-PD_{2,max}}{\sigma(R_2)}\right)^2\right]_{PD} \quad [6]$$

To ensure that $R_1$, $R_2$ and PD had the same weight in the cost function, the square of the residuals was normalised using the variance $\sigma^2$ of $R_1$, $R_2$ and PD.

The entire procedure was repeated, where each of the variable parameters was varied individually, with increasingly smaller steps until the minimum residual was found. To avoid convergence to a local minimum, this procedure was repeated 100 times, after which the lowest residual was regarded as the global minimum.

The confidence interval of the optimised parameters was calculated using the finite sample confidence intervals in the maximum likelihood. According to this approach the confidence region is found by varying a single parameter and minimising all others such that the cost function remains under the value of $\chi^2$(a, df), where a corresponds to the confidence level and df is the number of degrees of freedom. Using a=0.05 and df=5, the $\chi^2$(a, df) function becomes 9.488. The Bloch simulation and minimisation procedure was implemented in an in-house developed IDL program (ITT visual information solutions, Boulder, Colo., USA).

Calculation of Total Volumes and Regions of Interest

Segmentation of the intracranial volume (ICV) was performed using an automatic procedure in SyMRI 7.0. The total myelin volume, cellular volume, free water volume and excess parenchymal water volume were calculated by summing all partial volumes within the ICV. The brain parenchymal volume (BPV) was defined as the ICV minus the total free water volume. The brain parenchymal fraction (BPF) corresponds to BPV divided by ICV. The myelin fraction (MYF) was calculated as the total myelin volume divided by the BPV. Also, the cellular water fraction (CF) and excess parenchymal water fraction (EPWF) were calculated in a similar manner as the total cellular volume divided by the BPV and total excess parenchymal water volume divided by the BPV, respectively.

The Myelin Water Fraction (MWF) can be derived from the model parameters because the myelin water corresponds to the $PD_{MY}$ in the $V_{MY}$, and the intra- and extracellular water corresponds to the sum of $PD_{CL}$ and $PD_{EPW}$ in the $V_{CL}$ and $V_{EPW}$, such that MWF for each acquisition voxel can be calculated as $MWF=(V_{MY}*PD_{MY})/(V_{CL}*PD_{CL}+V_{EPW}*PD_{EPW})$. Additionally, the total aqueous content of the tissue can be calculated, corresponding to the sum of the myelin water, cellular water, free water and excess parenchymal water, $V_{MY}*PD_{MY}+V_{CL}*PD_{CL}+V_{FW}*PD_{FW}+V_{EPW}*PD_{EPW}$. The total non-aqueous content then corresponds to 100% minus the aqueous content.

To define regions of interest for the spatially normalized brain images, the cropped ROI templates, based on the Wake Forrest University (WFU) PickAtlas were taken (Ref 25, Table 2). To verify that the standard ROIs in spatially normalized, averaged brain images provide similar results as spatially non-normalized, separate brain images, 3×3 mm ROIs were manually placed in a subset of brain structures in all participants of Ref. 25. This was also done for the three example subjects. In the MS cases areas with MS lesions were avoided.

Results

Optimising the Model Parameters to the Healthy Brain

In FIG. 3, the $R_1$, $R_2$ and PD values for the spatially normalised brains of the group of controls are shown as 2D-histograms of $R_1$ and $R_2$, $R_1$ and PD and $R_2$ and PD. The colour scale indicates the number of voxels for each coordinate in the histogram. The black dots are placed at the maximum values of the histograms in each direction, generating the 600 maxima defining the structure in the $R_1$-$R_2$-PD space.

Using these 600 maxima, the six variables in the tissue model were optimised to find the minimum value of the cost function (See FIG. 2). The values of the parameters at the minimum residual (3.446) are given in Table 1. Each parameter was varied individually while re-optimising all others such that the cost function remained below 9.488, resulting in the determination of the standard deviations of the parameters, as also listed in Table 1.

Behaviour of the Model for the Pathological Brain

The mean values in Table 1 provide the relaxation parameters for the four partial volumes for the healthy brain. According to the tissue model all observed $R_1$, $R_2$ and PD values in the healthy brain can be reproduced by combinations of $V_{FW}$, $V_{CL}$ and $V_{MY}$ using these characteristics. This is indicated as the thick black curve in FIG. 4 showing the transition from 100% $V_{FW}$ at ($R_1$, $R_2$, PD)=(0.24 s$^{-1}$, 0.87 s$^{-1}$, 100%) to 100% $V_{CL}$ at ($R_1$, $R_2$, PD)=(0.78 s$^{-1}$, 10.3 s$^{-1}$, 85%), continuing toward 100% $V_{MY}$ at ($R_1$, $R_2$, PD)=(16.6 s$^{-1}$, 77 s$^{-1}$, 42%). In the figure the positions of 100% $V_{FW}$ and 100% $V_{CL}$ are indicated at the red dots labelled by 'FW' and 'CL', respectively. The 100% $V_{MY}$ position is outside the range of the plot, the grid is clipped at 40% $V_{MY}$.

For the pathological brain, two processes can occur in the model: (1) a decrease in $V_{MY}$ and (2) the presence of non-zero $V_{EPW}$. In FIG. 4 a grid is displayed, indicating steps of possible combinations of 5% difference of $V_{MY}$ and 10% difference of $V_{EPW}$. This grid spans a curved surface in the $R_1$-$R_2$-PD space. In the background of FIG. 4 the data for the spatially normalised brain for the MS group were plotted. It can be seen that the MS data values are shifted toward lower $R_1$ and $R_2$ and higher PD relative to the black curve, which was optimised using the healthy data values.

Modelling the Spatially Normalised Brain Images

The grid in FIG. 4 was used to relate the $R_1$, $R_2$ and PD values of the spatially normalised brain data to combinations of $V_{MY}$, $V_{CL}$, $V_{FW}$ and $V_{EPW}$. The result is shown in FIG. 5 for the spatially normalised brain images of the control and MS groups. The $V_{MY}$ is substantially higher for the controls than for the MS group. The total myelin volumes were 157 mL and 119 mL, respectively, a difference of 38 mL. Also, the total free water volume was visibly lower, at 65 mL for the control group versus 144 mL for the MS group, a difference of 79 mL. The intracranial volume of the spatially normalised datasets was 1213 mL for both groups, resulting in brain volumes of 1148 mL and 1069 mL, corresponding to a BPF of 94.6% and 88.1%, respectively. All volumes and volume fractions in relation to brain volume are provided in Table 2. The observed $R_1$, $R_2$ and PD values in the standard WFU PickAtlas ROIs of separate brain structures were used to calculate the local mean $V_{MY}$, $V_{CL}$ and $V_{EPW}$ of the spatially normalised control group and spatially normalised MS group (see Table 3). For the healthy group, $V_{MY}$ for the GM structures was in the range of 8-15% (average 14±3%), whereas that for WM structures was 18-27% (average 23±3%). For the MS group, $V_{MY}$ was 1-4% lower, with most of the difference in the WM structures; the average was 13±5% for GM structures (difference: 1.6±1.5%) and 20±3% for WM structures (difference: 2.8±1.0%). The mean $V_{CL}$ was 0-10% lower in the MS group. $V_{EPW}$ was higher in the MS group, with a difference of 9±10% and 5±2%, respectively, compared to the healthy group. Large differences were observed for the caudate nucleus, for which the MS group had a 28% lower $V_{CL}$ and 31% higher $V_{EPW}$ compared with the healthy group. For completeness, also the MWF was derived from the tissue model, which was 8.3±2.9% for GM structures and 14.4±2.3% for WM structures for the healthy group and 7.2±3.0% and 11.9±2.3%, respectively, for the MS group, a difference of 1.2±0.9% and 2.5±0.7%, respectively. The MWF values show the same trend as $V_{MY}$ but are substantially lower, 43% on average. For comparison, ROIs were manually placed in a subset of all brain structures for all participants in the study, using the original, spatially non-normalized brain images (Table 4). The differences between GM and WM structures are far more extreme in this case. For example, for the healthy group, the $V_{MY}$ for cortical GM decreases from 15% for the standard ROI to 2% for the manually placed ROI, whereas for the corpus callosum $V_{MY}$ increases from 27% to 41%. Most of the $V_{EPW}$ values decrease, except for the occipital WM (9%).

For the manual ROIs no significant differences were observed for the grey matter structures between the MS patients and the control group. For WM, however, $V_{MY}$ was 3% lower for occipital WM (p=0.04), 2% lower for frontal WM (p=0.04), and 5% lower for corpus callosum (p=0.02).

Modelling the High-Resolution Brain Images

In FIG. 6, the model was applied on high-resolution image datasets of a middle-aged (45y) and elderly control subject (72y) and an MS patient (45y-MS), in combination with a conventional FLAIR image (A). The $R_1$, $R_2$ and PD maps (B-D) demonstrate that the 72y (row 2) had generally lower $R_1$ and $R_2$ values and higher PD values throughout the brain than the 45y (row 1). For the 45y-MS (row 3), the $R_1$, $R_2$ and PD values were similar to those for the 45y, but much lower in the areas where the MS lesions were located. FIG. 6E presents the estimated $V_{MY}$, with a high $V_{MY}$ in the WM (33%, see Table 5) and low $V_{MY}$ in the GM (4%) for the 45y. The 72y showed less myelin throughout the brain than the 45y, with an average $V_{MY}$ of 26% in the WM Only the corpus callosum showed higher values (33%). The estimated total myelin volumes were 155 mL for the 45y, 142 mL for the 72y and 119 mL for the 45y-MS, corresponding to a MYF of 14.2%, 12.6% and 11.5%, respectively (see Table 2). The cellular fractions (FIG. 6F) were 83.7%, 83.7% and 84.9%, respectively. FIG. 6G presents $V_{FW}$, highlighting the ventricular system and periphery of the brain. Using the ICV and free water volume of the subjects, the BPV can be calculated, which was 1090 mL for the 45y, 1127 mL for the 72y and 1031 mL for the 45y-MS. Correspondingly, the BPF was 90.3%, 78.5% and 83.5%, respectively.

The 45y exhibited a small amount of $V_{EPW}$ (FIG. 6H), mainly around the occipital horns of the lateral ventricles, with a maximum of 11% in the occipital white matter. The 72y had elevated $V_{EPW}$ in the complete periventricular region, with values of up to 16% partial volume. The 45y-MS showed moderate $V_{EPW}$ values at the periventricular area and 12% in the occipital white matter. At the location of MS lesions however, high $V_{EPW}$ values, up to approximately 50% were observed. The $V_{EPW}$ volumes were 24 mL for the 45y, 41 mL for the 72y and 37 mL for the 45y-MS, corresponding to an EPWF of 2.2%, 3.5% and 3.6%, respectively.

The histograms of $V_{MY}$, $V_{CL}$, $V_{FW}$ and $V_{EPW}$ are shown in FIG. 7 to assess the distribution of the partial volumes of the three subjects. The histograms contain 100 bins from 0 to 100% partial volume and are plotted as a percentage of the ICV volume to compensate for the difference in subject head size. The 45y exhibited two peaks in the $V_{MY}$ histogram at 5% and 32% $V_{MY}$. For the 72y the peak $V_{MY}$ values occurred at 25%. The 45y-MS did not have a clear peak at higher $V_{MY}$ values. The $V_{CL}$ values peaked at 68 and 92% for the 45y, but only one peak was observed for both the 72y and 45y-MS at 89%. $V_{FW}$ values were generally low (<0.5%) in the complete range but exhibited a sharp peak at 100% $V_{FW}$, with a maximum of 3.7% for the 45y, 23.3% for the 72y and 11.9% for the 45y-MS. $V_{EPW}$ was observed in all three subjects, but the values were lowest for the 45y.

The area with the lesion of the MS patient, posterior to the left lateral ventricle, was zoomed out and displayed in FIG. 8, showing a FLAIR image together with $V_{MY}$, $V_{CL}$, $V_{FW}$ and $V_{EPW}$, taken from FIGS. 6A and E-H. At the location of the FLAIR hyper-intensity, the $V_{MY}$ was equal to zero, whereas the $V_{EPW}$ values were up to 55% partial volume. The diffuse hyper-intensity, located between the lesion and lateral ventricle, exhibited $V_{MY}$ values of 15-20% and $V_{EPW}$ values of 25-30% partial volume. Elevated $V_{EPW}$ values were observed in a large area around the lesion. The $V_{CL}$ varied only slightly, ranging between 45% at the lesion and 55% at the diffusely hyper-intense area.

Using the four partial volumes, the total aqueous content of the brain can be derived. The sum of all PD contributions of $V_{MY}$, $V_{CL}$, $V_{FW}$ and $V_{EPW}$ is shown in FIG. 9A for the 45y-MS, for the same slice as FIGS. 6 and 8. The centres of the MS lesions exhibit a total aqueous content of 85-95%, consisting entirely of the PD component of $V_{CL}$ and $V_{EPW}$. Normal appearing white matter for this patient showed a total aqueous content approximately 70%, consisting mainly of the PD component of $V_{MY}$ and $V_{CL}$, but also showing a minor contribution of $V_{EPW}$ in the order of 5%. Normal appearing grey matter shows a total aqueous content of approximately 85%, consisting largely of the PD component of $V_{CL}$, but with a small contribution of $V_{MY}$, up to 5%. The remaining non-aqueous content is shown in FIG. 9B.

The $R_1$, $R_2$ and PD values, as measured in the brain using a fast multi-parametric qMRI sequence, were modelled by four partial volume compartments per acquisition voxel, (1) the myelin partial volume $V_{MY}$, (2) cellular partial volume $V_{CL}$, (3) free water partial volume $V_{FW}$ and (4) excess parenchymal water partial volume $V_{EPW}$. The major advantage of this model is that it produces an estimate of three clinically relevant parameters, the total brain volume, the degree of myelination of the brain parenchyma and the degree of oedema of the brain parenchyma, based on a single, relatively short acquisition.

For a complex organ such as the brain, with an abundance of magnetically interacting microscopic substructures, MR signal relaxation will behave as a multitude of exponentials. Multi-component measurements, such as the multi-exponential $T_2$ relaxation and mcDESPOT approaches, typically regularise relaxation signals to force the solution into a fast component attributed to myelin water, a medium-time component attributed to intra- and extracellular water and occasionally in a long-time component attributed to CSF. Attempts to experimentally resolve the fast component, however, are very challenging. The qMRI sequence employed in this work cannot resolve the fast signal component, but can accurately measure the medium-time relaxation component. The estimation of myelin partial volume of the tissue model is therefore based on the shift of this medium-time component due to magnetisation exchange between myelin water and surrounding intra- and extracellular water. Such a shift is observable both in the $R_1$ and $R_2$ relaxation rates, thus building a specific pattern in the $R_1$-$R_2$-PD space, as visualised in FIG. 3 for a group of healthy controls and in FIG. 4 for a group of MS patients. Therefore, the tissue model relies on a combined $R_1$-$R_2$-PD measurement as a single component/multi-parametric quantification strategy, in contrast to the multi-component/single parametric quantification methods, such as e.g. the multi-component $T_2$ relaxation. The observed values for brain parenchyma of $R_1$ in the range of 0.9-1.9 s$^{-1}$ ($T_1$=530-1100 ms) and $R_2$ in the range of 10.5-13 s$^{-1}$ ($T_2$=75-95 ms) corresponded well with previously reported values for GM and WM, where other qMRI methods were used. Also, the measured PD corresponds well to the reported values with GM structures of 80-86% and WM of 74-76%.

The determined optimal parameter values for the partial volume compartments are listed in Table 1. The result of the optimization provides three specific coordinates in the $R_1$-$R_2$-PD space, for pure $V_{FW}$ (set by literature values to ($R_1$, $R_2$, PD)=(0.24 s$^{-1}$, 0.87 s$^{-1}$, 100%)), pure $V_{CL}$ (estimated at (0.78 s$^{-1}$, 10.3 s$^{-1}$, 85%)) and pure $V_{MY}$ (estimated at (16.6 s$^{-1}$, 77 s$^{-1}$, 42%)). The characteristics of the $V_{CL}$ are close to those of cortical GM. The characteristics of the $V_{MY}$ are within the range of previous reported values. Using the tissue model, the possible value combinations of $R_1$, $R_2$ and PD in the healthy brain were visualised by the solid black curve through the $R_1$-$R_2$-PD space, as plotted in FIG. 4. The difference between the healthy brain and pathological brain was described using two components: (1) the variation of the $V_{MY}$, indicating myelin loss, and (2) the presence of $V_{EPW}$, indicating the presence of oedema. These two components expanded the (healthy) curve to a curved surface grid, as shown in FIG. 4. Each observed value combination of $R_1$, $R_2$ and PD in acquisition voxels of a pathological brain is regarded as a combination of the $V_{MY}$, $V_{CL}$, $V_{FW}$ and $V_{EPW}$ partial volume compartments. As shown in FIG. 5, substantial differences were observed between the spatially normalised control group and spatially normalised MS group in all partial volumes. The MS group had a smaller $V_{MY}$ and $V_{CL}$ (a difference of 3.1% and 5.1% of the ICV, respectively) and larger $V_{FW}$ and $V_{EPW}$ (a difference of 6.5% and 1.7% of the ICV, respectively). Consequently, the average brain volume of the MS group was smaller than that of the control group (88.1% versus 94.6% of the ICV), the degree of myelination in the brain was lower (11.1% versus 13.7% of the BPV) and the degree of oedema in the brain was higher (7.3% versus 5.0% of the BPV). This result is congruent with knowledge concerning the disease progression of MS. The relative cellular volume in the brain was virtually identical (81.6% and 81.4%), as can be expected in a tissue model where oedema is described by a separate class of excess parenchymal water, which is an addition of water to the normal cellular partial volume. The values in Table 3 for the various brain structures confirm the image shown in FIG. 5.

The model was tested on three individual subjects as examples for high-resolution imaging. This can by no means be representative for entire groups of subjects and hence is purely used as example of the application of the model. Inclusion of larger groups to assess statistical differences with different age groups and diseases will be performed in future work. Clear differences were observed among the three subjects. Compared with the healthy controls, the $V_{MY}$ partial volume was lower for both the elderly subject and MS patient (FIG. 6). Additionally, the MS patient showed strong local decreases at the location of MS lesions. Similar to the spatially normalised brains of FIG. 5, the cellular fraction of the brain was virtually identical for all subjects. The $V_{FW}$ clearly highlights the CSF in the ventricular system and brain periphery, making it possible to calculate the brain volume of the subjects. The elderly subject had the smallest brain, with a BPF of 78.5%, compared with the 90.3% for the healthy 45y and 83.5% for the MS patient. Simultaneously the MS patient had the lowest myelination, with a MYF of 11.5%, compared with 14.2% for the healthy 45y and 12.6% for the 72y. In FIG. 7 the cause of the reduction can be attributed to a substantial loss of high $V_{MY}$ values for both the MS patient and 72y. The EPWF was substantially higher for the 72y and the 45y-MS compared with the healthy 45y. These findings are consistent with general myelin loss and oedema during aging and MS disease progression.

The behaviour of the partial volume components around the MS lesion of the 45y-MS, displayed in the zoomed sections shown in FIG. 8, is particularly interesting. The hyper-intensity on the FLAIR image has diffuse edges, making it difficult to estimate the exact volume of the lesion. However, on the $V_{MY}$ image, a clear centre, where the myelin has completely vanished, can be observed. At the same location, there is an elevation of the $V_{EPW}$, but this area is larger and decreases toward zero outwards. On a FLAIR image, no distinction can be made between oedema and myelin loss because both processes result in a hyper-intense signal. Using the model, on the other hand, the partial volume images indicate a demyelinated centre within a larger area of oedema. This example suggests that the model can distinguish between myelin loss and the presence of excess water in oedema. An interesting derivate of the model is the total aqueous content and the corresponding, remaining non-aqueous content. The used sequence cannot resolve the short $R_2$ relaxation component and therefore the observed PD value will correspond to the visible PD of the medium and long-time components. Using the observed shift in $R_1$ and $R_2$ the model can predict the presence of the myelin component and therefore the true PD value as would be measured at an echo time of zero. The non-aqueous content (FIG. 9B) can be attributed to the presence of macro-molecules in the brain. From the results it can be derived that the macromolecular content for the 45y-MS in the MS lesions was 15-5%, of normal appearing white matter approximately 30%, and of normal appearing grey matter approximately 15%.

In Table 2 the MWF is also listed, as directly derived from the tissue model PD values. The definitions of $V_{MY}$ and MWF are not identical; $V_{MY}$ is the estimated myelin fraction of an acquisition voxel based on the effective relaxation properties of that voxel, whereas MWF corresponds to the ratio of observable short-time relaxation (myelin) and medium-time relaxation (cellular) water content. The calculated MWF values are considerably lower than $V_{MY}$ (43% on average). The cause is that myelin water only covers a fraction of the total myelin volume, which also includes the (non-observable) myelin semi-solids. An issue may cause a difference between the observed MWF and the reported MWF values: Using the multi-echo $T_2$ relaxation in combination with the NNLS method, the magnetisation exchange, responsible for the shift of the medium-time component, is ignored. Such an exchange not only results in a shift of the medium-time component, but is also responsible for a simultaneous decrease in the short-time component. This will lead to a lower observed value for MWF. Studies measuring MWF using multi-exponential $T_2$ relaxation indeed reported lower values than the estimated MWF values, such as 7.0-10.1% in white matter, 3.6-5.6% in the putamen and 4.5-4.7% in the thalamus, compared with the values of 15, 9 and 12%, respectively (Table 3). In contrast, the mcDESPOT approach does account for magnetisation exchange and consequently exhibits considerably higher values of MWF. For example, the observed MWF values were as high as 28-30% for white matter, 11-13% for the putamen and 14-15% for the thalamus, which are more in the range of the estimated $V_{MY}$ values.

In conclusion, a tissue model is described above in which each MRI acquisition voxel in the brain is composed of a myelin partial volume, a cellular partial volume, a free water partial volume and an excess parenchymal water partial volume. Using this tissue model, clinically relevant information such as the brain volume, degree of myelination and degree of oedema, may be estimated based on an acquisition with a clinically acceptable scan time.

A method for estimating non-aqueous tissue volume of at least a portion of a subject is schematically disclosed in FIG. 10. The method comprises the following steps:

100: obtaining quantitative magnetic resonance properties of the portion of the subject, 101: providing the quantitative magnetic resonance properties as input to a tissue model, 102: determining, based on the tissue model and the quantitative magnetic resonance properties, the non-aqueous tissue volume of the portion.

The subject may be a human being and the portion being examined may be a volume portion of any part of the body such as an intracranial portion, a muscle portion, a portion of an internal organ and so on. As an example, a portion may be a cross sectional slice from a body part. A portion being examined may be of any size depending on the circumstances.

A device 1 for estimating non-aqueous tissue volume of at least a portion of a subject is schematically depicted in FIG. 11. A magnetic resonance imaging device 2 is used for obtaining quantitative magnetic resonance properties of an object such as a part of a human body. The imaging device 2 may be any device configured for image acquisition by magnetic resonance imaging. The imaging device 2 may generate cross-sectional images in any plane (including oblique planes) of the human body.

Preferably, the imaging device 2 is adapted to generate quantitative MRI scan results, i.e. measurements of physical properties such as $R_1$, $R_2$ and PD on an absolute scale.

The device 1 further comprises a processing unit 3 configured to obtain information from the magnetic resonance imaging device 2, process obtained information and determine several properties based on obtained information. The processing device may provide the obtained information as input to a tissue model. The device may also comprise a presentation unit 4 for presenting information to a user. The presentation unit may comprise a graphical user interface. Different kinds of information may be presented to a user depending on the circumstances.

Signalling within the device 1 may be performed by wire or wireless depending on the circumstances. The device may also be connected to other remote units such as user interface, servers, network connecting devices and so on. The processing unit may comprise a single main unit or a plurality of interconnected processing sub-units.

A non-transitory digital storage medium 4 is schematically depicted in FIG. 12. The storage medium 4 may comprise computer program instructions which can be executed by a computer. The computer may be any conventional computing device comprising processing means for executing computer program instructions. The storage medium may be comprised in a device such as the device 1 in FIG. 11 or it may be configured as a remote unit communicating with a device such as the device 1 in FIG. 11.

Tables

TABLE 1

The parameter values of the model; on the left the fixed parameters (see Materials and Methods); on the right, the optimized parameters where the cost function was minimized for the brain data of the control group (n = 20). The standard deviation of the latter values is given for a significance level of a = 0.05.

| Fixed parameters | Optimised parameters |
|---|---|
| $R_{2,MY}$ = 77 s$^{-1}$ | $R_{1,MY}$ = 16.6 ± 13.2 s$^{-1}$ |
| $R_{1,FW}$ = $R_{1,EPW}$ = 0.24 s$^{-1}$ | $PD_{MY}$ = 42 ± 33% |
| $R_{2,FW}$ = $R_{2,EPW}$ = 0.87 s$^{-1}$ | $k_{VMY-VCL}$ = 6.7 ± 5.2 s$^{-1}$ |
| $PD_{FW}$ = $PD_{EPW}$ = 100% | $R_{1,CL}$ = 0.78 ± 0.13 s$^{-1}$ |
| $k_{VEPW-VCL}$ = ∞ s$^{-1}$ | $R_{2,CL}$ = 10.3 ± 0.6 s$^{-1}$ |
| | $PD_{CL}$ = 85 ± 5% |

TABLE 2

The total volumes and volume fractions for the spatially normalized healthy control group and spatially normalized MS group of FIGS. 4 and 5 as well as for the three individual subjects of FIG. 6. Listed are the total myelin volume (MYV), cellular volume (CV), free water volume (FWV), excess parenchymal water volume (EPWV), total brain volume (BPV) and intracranial volume (ICV). The volume components that constitute the brain were normalized on BPV, resulting in the myelin fraction (MYF), cellular fraction (CF) and excess parenchymal water fraction (EPWF) of the brain.

| | MYV (mL) | CV (mL) | FWV (mL) | EPWV (mL) | BPV (mL) | ICV (mL) | MYF (%) | CF (%) | EPWF (%) |
|---|---|---|---|---|---|---|---|---|---|
| Control | 157 | 934 | 65 | 57 | 1148 | 1213 | 13.7 | 81.4 | 5.0 |
| MS | 119 | 872 | 144 | 78 | 1069 | 1213 | 11.1 | 81.6 | 7.3 |
| 45 y | 155 | 911 | 117 | 24 | 1090 | 1207 | 14.2 | 83.6 | 2.2 |
| 72 y | 142 | 944 | 308 | 41 | 1127 | 1435 | 12.6 | 83.7 | 3.7 |
| 45 y-MS | 119 | 875 | 204 | 37 | 1031 | 1234 | 11.5 | 84.9 | 3.6 |

TABLE 3

The mean myelin partial volume $V_{MY}$, cellular partial volume $V_{CL}$ and the excess parenchymal water partial volume $V_{EPW}$ of various brain structures, estimated as a percentage of the acquisition voxel volume. The values were calculated using the example model and the reported relaxation rates $R_1$ and $R_2$ and proton density PD in the WFU Pickatlas ROIs of the spatially normalized, averaged group of healthy controls and the spatially normalized, averaged group of multiple sclerosis patients from Ref. 25 (Table 2, cropped ROI templates). Added are the expected myelin water fraction MWF values, calculated as $PD_{MY}/(PD_{CL} + PD_{EPW})$.

|  | Healthy controls | | | | Multiple Sclerosis patients | | | |
|---|---|---|---|---|---|---|---|---|
|  | $V_{MY}$ (%) | $V_{CL}$ (%) | $V_{EPW}$ (%) | MWF (%) | $V_{MY}$ (%) | $V_{CL}$ (%) | $V_{EPW}$ (%) | MWF (%) |
| Insula | 8 | 75 | 17 | 4 | 8 | 66 | 26 | 4 |
| Cingulate cortex | 12 | 81 | 7 | 7 | 8 | 78 | 14 | 4 |
| Caudate nucleus | 9 | 87 | 4 | 5 | 6 | 59 | 35 | 3 |
| Cortical grey matter | 15 | 74 | 11 | 9 | 14 | 66 | 20 | 8 |
| Pons | 18 | 69 | 13 | 11 | 17 | 60 | 23 | 10 |
| Putamen | 15 | 85 | 0 | 9 | 15 | 85 | 0 | 9 |
| Mid brain | 19 | 81 | 0 | 12 | 18 | 79 | 3 | 11 |
| Thalamus | 19 | 81 | 0 | 12 | 16 | 84 | 0 | 9 |
| Occipital white matter | 18 | 82 | 0 | 11 | 15 | 83 | 2 | 9 |
| Frontal white matter | 21 | 77 | 2 | 14 | 19 | 73 | 8 | 11 |
| Parietal white matter | 21 | 77 | 2 | 14 | 19 | 73 | 8 | 11 |
| Sub-lobar white matter | 25 | 66 | 9 | 16 | 21 | 65 | 14 | 13 |
| White matter | 23 | 75 | 2 | 15 | 19 | 73 | 8 | 11 |
| Corpus callosum | 27 | 60 | 13 | 18 | 25 | 55 | 20 | 16 |

TABLE 4

The mean myelin partial volume $V_{MY}$, cellular partial volume $V_{CL}$ and the excess parenchymal water partial volume $V_{EPW}$ of various brain structures, estimated as a percentage of the acquisition voxel volume. The values were calculated using the example model and the relaxation rates $R_1$ and $R_2$ and proton density PD in manually placed ROIs in all participants of Ref. 25. Added are the expected myelin water fraction MWF values, calculated as $PD_{MY}/(PD_{CL} + PD_{EPW})$.

|  | Healthy controls | | | | Multiple Sclerosis patients | | | |
|---|---|---|---|---|---|---|---|---|
|  | $V_{MY}$ (%) | $V_{CL}$ (%) | $V_{EPW}$ (%) | MWF (%) | $V_{MY}$ (%) | $V_{CL}$ (%) | $V_{EPW}$ (%) | MWF (%) |
| Cingulate cortex | 2 | 96 | 2 | 1 | 2 | 95 | 3 | 1 |
| Caudate nucleus | 8 | 92 | 0 | 4 | 9 | 91 | 0 | 5 |
| Cortical grey matter | 2 | 95 | 3 | 1 | 2 | 95 | 3 | 1 |
| Putamen | 11 | 89 | 0 | 6 | 10 | 90 | 0 | 5 |
| Thalamus | 19 | 81 | 0 | 12 | 15 | 84 | 1 | 9 |
| Occipital white matter | 34 | 57 | 9 | 25 | 31 | 61 | 8 | 22 |
| Frontal white matter | 36 | 62 | 2 | 28 | 34 | 64 | 2 | 25 |
| Corpus callosum | 41 | 56 | 3 | 35 | 36 | 60 | 4 | 29 |

TABLE 5

The mean myelin partial volume $V_{MY}$, cellular partial volume $V_{CL}$, the excess parenchymal water partial volume $V_{EPW}$ and myelin water fraction MWF of various brain structures, estimated as a percentage of the acquisition voxel volume for the three example subjects.

|  | 45 y | | | | 72 y | | | | 45 y-MS | | | |
|---|---|---|---|---|---|---|---|---|---|---|---|---|
|  | $V_{MY}$ (%) | $V_{CL}$ (%) | $V_{EPW}$ (%) | MWF (%) | $V_{MY}$ (%) | $V_{CL}$ (%) | $V_{EPW}$ (%) | MWF (%) | $V_{MY}$ (%) | $V_{CL}$ (%) | $V_{EPW}$ (%) | MWF (%) |
| Insula | 4 | 95 | 1 | 2 | 3 | 91 | 6 | 2 | 7 | 92 | 1 | 4 |
| Cingulate cortex | 4 | 95 | 1 | 2 | 6 | 91 | 3 | 3 | 2 | 93 | 5 | 1 |
| Caudate nucleus | 13 | 87 | 0 | 7 | 9 | 91 | 0 | 5 | 10 | 90 | 0 | 5 |
| Cortical grey matter | 3 | 94 | 3 | 2 | 7 | 91 | 2 | 4 | 4 | 93 | 3 | 2 |
| Pons | 23 | 76 | 1 | 15 | 22 | 76 | 2 | 14 | 22 | 78 | 0 | 14 |
| Putamen | 11 | 89 | 0 | 6 | 9 | 91 | 0 | 5 | 12 | 88 | 0 | 7 |
| Mid brain | 19 | 81 | 0 | 12 | 18 | 79 | 3 | 11 | 21 | 78 | 1 | 13 |
| Thalamus | 19 | 81 | 0 | 12 | 20 | 79 | 1 | 12 | 21 | 79 | 0 | 13 |
| Occipital white matter | 31 | 58 | 11 | 22 | 27 | 57 | 16 | 18 | 32 | 56 | 12 | 23 |
| Frontal white matter | 35 | 60 | 5 | 26 | 25 | 61 | 14 | 16 | 36 | 62 | 2 | 27 |
| Parietal white matter | 35 | 61 | 4 | 26 | 26 | 70 | 4 | 17 | 35 | 64 | 1 | 27 |
| Sub-lobar white matter | 32 | 63 | 5 | 23 | 21 | 75 | 4 | 13 | 30 | 70 | 0 | 21 |
| White matter | 33 | 59 | 8 | 24 | 26 | 72 | 12 | 15 | 32 | 61 | 7 | 24 |
| Corpus callosum | 31 | 63 | 6 | 22 | 33 | 60 | 7 | 24 | 33 | 54 | 13 | 24 |

What is claimed is:

1. A method for estimating non-aqueous tissue volume of at least a portion of a subject, the method comprising:
obtaining, with a processor, quantitative magnetic resonance properties of the portion of the subject, the magnetic resonance properties of the portion of the subject including at least a longitudinal relaxation rate (R1) and a transverse relaxation rate (R2), and a proton density (PD) for the portion,
providing, with the processor, the quantitative magnetic resonance properties as input to a tissue model, and
determining, with the processor and based on the tissue model and the quantitative magnetic resonance properties, the non-aqueous tissue volume of the portion,
wherein the tissue model comprises at least three volume compartments including a free water partial compartment, a cellular tissue partial volume compartment, and a myelin tissue partial volume compartment.

2. The method according to claim 1, wherein determining the non-aqueous tissue volume comprises:
determining at least one partial volume compartment within the portion, and
determining a non-aqueous tissue partial volume present within each partial volume compartment, and
determining the non-aqueous tissue volume by adding up all said non-aqueous tissue partial volumes, or
determining an aqueous partial volume present within each partial volume compartment, and
determining a total aqueous volume by adding up all said aqueous partial volumes, and
determining the non-aqueous tissue volume by subtracting the total aqueous volume from a total volume of the portion.

3. The method according to claim 2, wherein the partial volume compartment comprises free water, excess parenchymal water, cellular tissue or myelin tissue.

4. The method according to claim 1, further comprising providing a reference value and comparing the non-aqueous tissue volume to the reference value.

5. The method according to claim 2, wherein determining the partial volume compartment, comprises determining:
a fraction of the partial volume compartment present in the portion.

6. The method according to claim 1, wherein the quantitative magnetic resonance properties are determined simultaneously in a single magnetic resonance acquisition.

7. The method according to claim 1, further comprising, in the processor, multiplying the determined non-aqueous tissue volume with a reference factor to obtain a hydration-corrected tissue volume.

8. The method according to claim 7, wherein the reference factor is determined based on a number of obtained reference values from a group of reference subjects.

9. The method according to claim 1, further comprising:
determining a tissue fraction by dividing the non-aqueous tissue volume by the total volume of the portion.

10. A device for estimating non-aqueous tissue volume of at least a portion of a subject, the device comprising:
a magnetic resonance imaging device for obtaining quantitative magnetic resonance properties of at least a portion of a subject, and
a processor configured to:
obtain quantitative magnetic resonance properties of the portion of the subject, the magnetic resonance properties of the portion of the subject including at least a longitudinal relaxation rate (R1) and a transverse relaxation rate (R2), and a proton density (PD) for the portion,
provide the quantitative magnetic resonance properties as input to a tissue model, and
determine, based on the tissue model and the quantitative magnetic resonance properties, the non-aqueous tissue volume of the portion,
wherein the tissue model comprises at least three volume compartments including a free water partial compartment, a cellular tissue partial volume compartment, and a myelin tissue partial volume compartment.

11. The device according to claim 10, wherein the processor is further configured to:
determine at least one partial volume compartment within the portion, and
determine a non-aqueous tissue partial volume present within each partial volume compartment, and
determine the non-aqueous tissue volume by adding up all said non-aqueous tissue partial volumes, or
determine an aqueous partial volume present within each partial volume compartment, and
determine a total aqueous volume by adding up all said aqueous partial volumes, and
determine the non-aqueous tissue volume by subtracting the total aqueous volume from a total volume of the portion.

12. The device according to claim 11, wherein the processor, when determining the partial volume compartment, is further configured to determine:
a fraction of the partial volume compartment present in the portion.

13. The device according to claim 10, wherein the quantitative magnetic resonance properties are determined simultaneously in a single magnetic resonance acquisition by the magnetic resonance imaging device.

14. The device according to claim 10, wherein the processor is further configured to multiply the obtained non-aqueous tissue volume with a reference factor to obtain a hydration-corrected tissue volume.

15. The device according to claim 14, wherein the processor is further configured to determine the reference factor based on a number of obtained reference values from a group of reference subjects.

16. The device according to claim 10, wherein the processor is further configured to determine a tissue fraction by dividing the non-aqueous tissue volume by the total volume of the portion.

17. The device according to claim 10, further comprising an interface configured to present information to a user.

18. A non-transitory digital storage medium having stored there on computer program instructions that, when executed by a computer, cause the computer to perform a method comprising:
obtaining quantitative magnetic resonance properties of the portion of the subject, the magnetic resonance properties of the portion of the subject including at least a longitudinal relaxation rate (R1) and a transverse relaxation rate (R2), and a proton density (PD) for the portion,
providing the quantitative magnetic resonance properties as input to a tissue model, and
determining, based on the tissue model and the quantitative magnetic resonance properties, the non-aqueous tissue volume of the portion,
wherein the tissue model comprises at least three volume compartments including a free water partial compartment, a cellular tissue partial volume compartment, and a myelin tissue partial volume compartment.

* * * * *